United States Patent
Radhakrishnan et al.

(10) Patent No.: US 7,985,252 B2
(45) Date of Patent: Jul. 26, 2011

(54) BIOERODIBLE ENDOPROSTHESIS

(75) Inventors: Rajesh Radhakrishnan, Maple Grove, MN (US); Chandru Chandrasekaran, Mercer Island, WA (US); Scott R. Schewe, Eden Prairie, MN (US); Ken Merdan, Loretto, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 18 days.

(21) Appl. No.: 12/182,768

(22) Filed: Jul. 30, 2008

(65) Prior Publication Data

US 2010/0030326 A1 Feb. 4, 2010

(51) Int. Cl.
*A61F 2/24* (2006.01)

(52) U.S. Cl. .............. 623/1.46; 623/1.38; 623/1.44

(58) Field of Classification Search .............. 623/1.11, 623/1.13, 1.15, 1.39, 1.42, 1.44, 1.45, 1.46, 623/1.38
See application file for complete search history.

(56) References Cited

U.S. PATENT DOCUMENTS

| | | | |
|---|---|---|---|
| 2,950,187 A | 8/1960 | Ototani |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |
| 4,655,771 A | 4/1987 | Wallsten |

(Continued)

FOREIGN PATENT DOCUMENTS

AU      739 507      11/1998

(Continued)

OTHER PUBLICATIONS

Kutsenko et al., "Structural changes in Mg alloy induced by plasma immersion ion implantation of Ag," *Acta Materialia*, 2004, 52:4329-4335.

(Continued)

*Primary Examiner* — David Isabella
*Assistant Examiner* — Seema Swaminathan
(74) *Attorney, Agent, or Firm* — Fish & Richardson P.C.

(57) ABSTRACT

An endoprosthesis includes a plurality of struts defining a flow passage. At least one strut includes (a) a body comprising a bioerodible material and having a thickness and (b) a coating overlying the body. The coating includes a plurality of regions that allow physiological fluids to contact a plurality of corresponding areas of the underlying body when the endoprosthesis is implanted in a physiological environment. The plurality of regions are sized and arranged so that the contacted areas of the body erode substantially through the body in the thickness direction while the coating remains on the body when the endoprosthesis is implanted in the physiological environment.

19 Claims, 6 Drawing Sheets

U.S. PATENT DOCUMENTS

| | | |
|---|---|---|
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |
| 4,784,659 A | 11/1988 | Fleckenstein et al. |
| 4,800,882 A | 1/1989 | Gianturco |
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,024,671 A | 6/1991 | Tu et al. |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang et al. |
| 5,205,921 A | 4/1993 | Shirkanzadeh |
| 5,234,457 A | 8/1993 | Andersen |
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |
| 5,306,286 A | 4/1994 | Stack et al. |
| 5,314,453 A | 5/1994 | Jeutter |
| 5,322,520 A | 6/1994 | Milder |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,500,013 A | 3/1996 | Buscemi et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A | 12/1996 | Lorenz et al. |
| 5,587,507 A | 12/1996 | Kohn et al. |
| 5,591,222 A | 1/1997 | Susawa et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnlund et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,674,192 A | 10/1997 | Sahatjian et al. |
| 5,674,242 A | 10/1997 | Phan et al. |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,761,775 A | 6/1998 | Legome et al. |
| 5,769,883 A | 6/1998 | Buscemi et al. |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,907,893 A | 6/1999 | Zadno-Azizi et al. |
| 5,922,021 A | 7/1999 | Jang |
| 5,928,247 A | 7/1999 | Barry et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |
| 5,976,454 A | 11/1999 | Sterzel et al. |
| 5,977,204 A | 11/1999 | Boyan et al. |

| | | | |
|---|---|---|---|
| 5,980,554 A | 11/1999 | Lenker et al. | |
| 5,980,564 A | 11/1999 | Stinson | |
| 5,980,566 A | 11/1999 | Alt et al. | |
| 6,001,125 A | 12/1999 | Golds et al. | |
| 6,013,591 A | 1/2000 | Ying et al. | |
| 6,017,553 A | 1/2000 | Burrell et al. | |
| 6,017,577 A | 1/2000 | Hostettler et al. | |
| 6,021,347 A | 2/2000 | Herbst et al. | |
| 6,025,036 A | 2/2000 | McGill et al. | |
| 6,027,742 A | 2/2000 | Lee et al. | |
| 6,034,295 A | 3/2000 | Rehberg et al. | |
| 6,063,101 A | 5/2000 | Jacobsen et al. | |
| 6,071,305 A | 6/2000 | Brown et al. | |
| 6,080,190 A | 6/2000 | Schwartz | |
| 6,086,773 A | 7/2000 | Dufresne et al. | |
| 6,096,070 A | 8/2000 | Ragheb et al. | |
| 6,096,175 A | 8/2000 | Roth | |
| 6,099,561 A | 8/2000 | Alt | |
| 6,099,562 A | 8/2000 | Ding et al. | |
| 6,106,473 A | 8/2000 | Violante et al. | |
| 6,107,004 A | 8/2000 | Donadio, III | |
| 6,117,592 A | 9/2000 | Hoshino et al. | |
| 6,120,535 A | 9/2000 | McDonald et al. | |
| 6,120,660 A | 9/2000 | Chu et al. | |
| 6,123,861 A | 9/2000 | Santini, Jr. et al. | |
| 6,132,463 A | 10/2000 | Lee et al. | |
| 6,139,573 A | 10/2000 | Sogard et al. | |
| 6,139,574 A | 10/2000 | Vacanti et al. | |
| 6,139,913 A | 10/2000 | Van Steenkiste et al. | |
| 6,140,740 A | 10/2000 | Porat et al. | |
| 6,143,370 A | 11/2000 | Panagiotou et al. | |
| 6,153,252 A | 11/2000 | Hossainy et al. | |
| 6,159,142 A | 12/2000 | Alt | |
| 6,162,238 A | 12/2000 | Kaplan et al. | |
| 6,164,284 A | 12/2000 | Schulman et al. | |
| 6,165,211 A | 12/2000 | Thompson | |
| 6,167,307 A | 12/2000 | Hess | |
| 6,168,602 B1 | 1/2001 | Ryan | |
| 6,170,488 B1 | 1/2001 | Spillman, Jr. et al. | |
| 6,174,329 B1 | 1/2001 | Callol et al. | |
| 6,174,330 B1 | 1/2001 | Stinson | |
| 6,180,222 B1 | 1/2001 | Schulz et al. | |
| 6,185,455 B1 | 2/2001 | Loeb et al. | |
| 6,185,457 B1 | 2/2001 | Kroll et al. | |
| 6,190,404 B1 | 2/2001 | Palmaz et al. | |
| 6,192,271 B1 | 2/2001 | Hayman | |
| 6,201,991 B1 | 3/2001 | Chekanov | |
| 6,203,536 B1 | 3/2001 | Berg et al. | |
| 6,206,914 B1 | 3/2001 | Soykan et al. | |
| 6,206,915 B1 | 3/2001 | Fagan et al. | |
| 6,206,916 B1 | 3/2001 | Furst | |
| 6,212,434 B1 | 4/2001 | Scheiner et al. | |
| 6,214,037 B1 | 4/2001 | Mitchell et al. | |
| 6,214,042 B1 | 4/2001 | Jacobsen et al. | |
| 6,217,607 B1 | 4/2001 | Alt | |
| 6,240,616 B1 | 6/2001 | Yan | |
| 6,241,762 B1 | 6/2001 | Shanley | |
| 6,245,103 B1 | 6/2001 | Stinson | |
| 6,245,104 B1 | 6/2001 | Alt | |
| 6,249,952 B1 | 6/2001 | Ding | |
| 6,251,136 B1 | 6/2001 | Guruwaiya et al. | |
| 6,251,980 B1 | 6/2001 | Lan et al. | |
| 6,253,252 B1 | 6/2001 | Schofield | |
| 6,253,443 B1 | 7/2001 | Johnson | |
| 6,254,632 B1 | 7/2001 | Wu et al. | |
| 6,258,117 B1 | 7/2001 | Camrud et al. | |
| 6,270,831 B2 | 8/2001 | Kumar et al. | |
| 6,273,908 B1 | 8/2001 | Ndondo-Lay | |
| 6,273,913 B1 | 8/2001 | Wright et al. | |
| 6,277,078 B1 | 8/2001 | Porat et al. | |
| 6,280,385 B1 | 8/2001 | Melzer et al. | |
| 6,280,411 B1 | 8/2001 | Lennox | |
| 6,283,386 B1 | 9/2001 | Van Steenkiste et al. | |
| 6,287,331 B1 | 9/2001 | Heath | |
| 6,287,332 B1 | 9/2001 | Bolz et al. | |
| 6,287,335 B1 | 9/2001 | Drasler et al. | |
| 6,287,628 B1 | 9/2001 | Hossainy et al. | |
| 6,290,721 B1 | 9/2001 | Heath | |
| 6,290,722 B1 | 9/2001 | Wang | |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,379 B1 | 4/2002 | Wang |
| 6,379,382 B1 | 4/2002 | Yang et al. |
| 6,379,383 B1 | 4/2002 | Palmaz et al. |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Bulrge et al. |
| 6,395,326 B1 | 5/2002 | Castro et al. |
| 6,398,806 B1 | 6/2002 | You |
| 6,419,692 B1 | 7/2002 | Yang et al. |
| 6,423,092 B2 | 7/2002 | Datta et al. |
| 6,436,133 B1 | 8/2002 | Furst et al. |
| 6,440,166 B1 | 8/2002 | Kolluri |
| 6,440,487 B1 | 8/2002 | Delfino et al. |
| 6,447,540 B1 | 9/2002 | Fontaine et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,589,286 B1 | 7/2003 | Litner |
| 6,599,558 B1 | 7/2003 | Al-Lamee et al. |

| Patent | Date | Inventor |
|---|---|---|
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B1 | 4/2004 | Raeder-Devens et al. |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B2 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |
| 7,018,408 B2 | 3/2006 | Bailey et al. |
| 7,022,334 B1 | 4/2006 | Ding et al. |
| 7,041,130 B2 | 5/2006 | Santini, Jr. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,077,859 B2 | 7/2006 | Sirhan et al. |
| 7,078,108 B2 | 7/2006 | Zhang et al. |
| 7,099,091 B2 | 8/2006 | Taniguchi et al. |

| | | |
|---|---|---|
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 | 1/2007 | Kramer |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen |
| 7,294,409 B2 | 11/2007 | Lye et al. |
| 7,311,727 B2 | 12/2007 | Mazumder et al. |
| 7,323,189 B2 | 1/2008 | Pathak |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,691,401 B2 | 4/2010 | Castro et al. |
| 7,713,297 B2 | 5/2010 | Alt |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1 | 1/2002 | Heublein et al. |
| 2002/0007102 A1 | 1/2002 | Salmon et al. |
| 2002/0007209 A1 | 1/2002 | Scheerder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0183682 A1 | 12/2002 | Torchia et al. |
| 2002/0187260 A1 | 12/2002 | Sheppard, Jr. et al. |
| 2002/0193336 A1 | 12/2002 | Elkins et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |
| 2003/0077200 A1 | 4/2003 | Craig et al. |
| 2003/0077310 A1 | 4/2003 | Pathak et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0099684 A1 | 5/2003 | Domb |
| 2003/0100815 A1 | 5/2003 | Da Silva et al. |
| 2003/0100830 A1 | 5/2003 | Zhong et al. |
| 2003/0104030 A1 | 6/2003 | Igaki et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118692 A1 | 6/2003 | Wang et al. |
| 2003/0120339 A1 | 6/2003 | Banik et al. |
| 2003/0124055 A1 | 7/2003 | Li et al. |
| 2003/0125803 A1 | 7/2003 | Vallana |
| 2003/0130718 A1 | 7/2003 | Palmas et al. |

| | | | | | | |
|---|---|---|---|---|---|---|
| 2003/0139799 A1 | 7/2003 | Ley et al. | | 2004/0181278 A1 | 9/2004 | Tseng et al. |
| 2003/0143330 A1 | 7/2003 | Loomis et al. | | 2004/0182511 A1 | 9/2004 | Rakos et al. |
| 2003/0144728 A1 | 7/2003 | Scheuermann et al. | | 2004/0186553 A1 | 9/2004 | Yan |
| 2003/0150380 A1 | 8/2003 | Yoe | | 2004/0191293 A1 | 9/2004 | Claude |
| 2003/0153901 A1 | 8/2003 | Herweck et al. | | 2004/0191404 A1 | 9/2004 | Hossainy et al. |
| 2003/0158598 A1 | 8/2003 | Ashton et al. | | 2004/0202692 A1 | 10/2004 | Shanley et al. |
| 2003/0170605 A1 | 9/2003 | Long et al. | | 2004/0204750 A1 | 10/2004 | Dinh |
| 2003/0181975 A1 | 9/2003 | Ishii et al. | | 2004/0211362 A1 | 10/2004 | Castro et al. |
| 2003/0185895 A1 | 10/2003 | Lanphere | | 2004/0219214 A1 | 11/2004 | Gravett et al. |
| 2003/0190406 A1 | 10/2003 | Hossainy et al. | | 2004/0220510 A1 | 11/2004 | Koullick et al. |
| 2003/0195613 A1 | 10/2003 | Curcio et al. | | 2004/0220659 A1 | 11/2004 | Girton |
| 2003/0204239 A1 | 10/2003 | Carlyle et al. | | 2004/0220660 A1 | 11/2004 | Shanley et al. |
| 2003/0211135 A1 | 11/2003 | Greenhalgh et al. | | 2004/0220662 A1 | 11/2004 | Dang et al. |
| 2003/0216803 A1 | 11/2003 | Ledergerber | | 2004/0224001 A1 | 11/2004 | Pacetti et al. |
| 2003/0219562 A1 | 11/2003 | Rypacek et al. | | 2004/0225346 A1 | 11/2004 | Mazumder et al. |
| 2003/0221307 A1 | 12/2003 | Kaese et al. | | 2004/0228905 A1 | 11/2004 | Greenspan et al. |
| 2003/0228523 A1 | 12/2003 | DeLongchamp et al. | | 2004/0230176 A1 | 11/2004 | Shanahan et al. |
| 2003/0236513 A1 | 12/2003 | Schwarz et al. | | 2004/0230225 A1 | 11/2004 | Penner et al. |
| 2004/0000046 A1 | 1/2004 | Stinson | | 2004/0230290 A1 | 11/2004 | Weber et al. |
| 2004/0000540 A1 | 1/2004 | Soboyejo et al. | | 2004/0230293 A1 | 11/2004 | Yip et al. |
| 2004/0006382 A1 | 1/2004 | Sohier | | 2004/0234737 A1 | 11/2004 | Pacetti |
| 2004/0018296 A1 | 1/2004 | Castro et al. | | 2004/0236415 A1 | 11/2004 | Thomas |
| 2004/0019376 A1 | 1/2004 | Alt | | 2004/0236416 A1 | 11/2004 | Falotico |
| 2004/0022939 A1 | 2/2004 | Kim et al. | | 2004/0237282 A1 | 12/2004 | Hines |
| 2004/0024448 A1 | 2/2004 | Chang et al. | | 2004/0242106 A1 | 12/2004 | Rabasco et al. |
| 2004/0029303 A1 | 2/2004 | Hart et al. | | 2004/0243217 A1 | 12/2004 | Andersen |
| 2004/0030218 A1 | 2/2004 | Kocur et al. | | 2004/0243237 A1 | 12/2004 | Unwin et al. |
| 2004/0034409 A1 | 2/2004 | Heublein et al. | | 2004/0243241 A1 | 12/2004 | Istephanous et al. |
| 2004/0039438 A1 | 2/2004 | Alt | | 2004/0247671 A1 | 12/2004 | Prescott et al. |
| 2004/0039441 A1 | 2/2004 | Rowland et al. | | 2004/0249440 A1 | 12/2004 | Bucker et al. |
| 2004/0044397 A1 | 3/2004 | Stinson | | 2004/0249443 A1 | 12/2004 | Shanley et al. |
| 2004/0047980 A1 | 3/2004 | Pacetti et al. | | 2004/0249444 A1 | 12/2004 | Reiss |
| 2004/0059407 A1 | 3/2004 | Escamilla et al. | | 2004/0249445 A1 | 12/2004 | Rosenthal et al. |
| 2004/0059409 A1 | 3/2004 | Stenzel | | 2004/0249449 A1 | 12/2004 | Shanley et al. |
| 2004/0067301 A1 | 4/2004 | Ding | | 2004/0254419 A1 | 12/2004 | Wang et al. |
| 2004/0071861 A1 | 4/2004 | Mandrusov et al. | | 2004/0254635 A1 | 12/2004 | Shanley et al. |
| 2004/0073155 A1 | 4/2004 | Laufer et al. | | 2005/0004661 A1 | 1/2005 | Lewis et al. |
| 2004/0073284 A1 | 4/2004 | Bates et al. | | 2005/0010275 A1 | 1/2005 | Sahatjian |
| 2004/0073293 A1 | 4/2004 | Thompson | | 2005/0010279 A1 | 1/2005 | Tenerz et al. |
| 2004/0073297 A1 | 4/2004 | Rohde et al. | | 2005/0015142 A1 | 1/2005 | Austin et al. |
| 2004/0073298 A1 | 4/2004 | Hossainy | | 2005/0019265 A1 | 1/2005 | Hammer et al. |
| 2004/0078071 A1 | 4/2004 | Escamilla et al. | | 2005/0019371 A1 | 1/2005 | Anderson et al. |
| 2004/0082682 A1 | 4/2004 | Loomis et al. | | 2005/0021127 A1 | 1/2005 | Kawula |
| 2004/0088038 A1 | 5/2004 | Dehnad et al. | | 2005/0021128 A1 | 1/2005 | Nakahama et al. |
| 2004/0088041 A1 | 5/2004 | Stanford | | 2005/0022627 A1 | 2/2005 | Chen |
| 2004/0093071 A1 | 5/2004 | Jang | | 2005/0027350 A1 | 2/2005 | Momma et al. |
| 2004/0093075 A1 | 5/2004 | Kuehne | | 2005/0033407 A1 | 2/2005 | Weber et al. |
| 2004/0093076 A1 | 5/2004 | White et al. | | 2005/0033411 A1 | 2/2005 | Wu et al. |
| 2004/0098089 A1 | 5/2004 | Weber | | 2005/0033412 A1 | 2/2005 | Wu et al. |
| 2004/0098108 A1 | 5/2004 | Harder et al. | | 2005/0033417 A1 | 2/2005 | Borges et al. |
| 2004/0098119 A1 | 5/2004 | Wang | | 2005/0037047 A1 | 2/2005 | Song |
| 2004/0106975 A1 | 6/2004 | Solovay et al. | | 2005/0037050 A1 | 2/2005 | Weber |
| 2004/0106984 A1 | 6/2004 | Stinson | | 2005/0038134 A1 | 2/2005 | Loomis et al. |
| 2004/0106985 A1 | 6/2004 | Jang | | 2005/0038501 A1 | 2/2005 | Moore, Jr. et al. |
| 2004/0111150 A1 | 6/2004 | Berg et al. | | 2005/0042288 A1 | 2/2005 | Koblish et al. |
| 2004/0116999 A1 | 6/2004 | Ledergerber | | 2005/0042440 A1 | 2/2005 | Bach et al. |
| 2004/0117005 A1 | 6/2004 | Gadde et al. | | 2005/0055044 A1 | 3/2005 | Kangas |
| 2004/0117008 A1 | 6/2004 | Wnendt et al. | | 2005/0055080 A1 | 3/2005 | Istephanous et al. |
| 2004/0122504 A1 | 6/2004 | Hogendijk | | 2005/0055085 A1 | 3/2005 | Rivron et al. |
| 2004/0126566 A1 | 7/2004 | Axen et al. | | 2005/0060020 A1 | 3/2005 | Jenson |
| 2004/0133270 A1 | 7/2004 | Grandt | | 2005/0060021 A1 | 3/2005 | O'Brien et al. |
| 2004/0134886 A1 | 7/2004 | Wagner et al. | | 2005/0064088 A1 | 3/2005 | Fredrickson |
| 2004/0137039 A1 | 7/2004 | Sukhishvili et al. | | 2005/0069630 A1 | 3/2005 | Fox et al. |
| 2004/0138738 A1 | 7/2004 | Stinson | | 2005/0070989 A1 | 3/2005 | Lye et al. |
| 2004/0142014 A1 | 7/2004 | Litvack et al. | | 2005/0070990 A1 | 3/2005 | Stinson |
| 2004/0143317 A1 | 7/2004 | Stinson et al. | | 2005/0070996 A1 | 3/2005 | Dinh et al. |
| 2004/0143321 A1 | 7/2004 | Litvack et al. | | 2005/0071016 A1 | 3/2005 | Hausdorf et al. |
| 2004/0148010 A1 | 7/2004 | Rush | | 2005/0072544 A1 | 4/2005 | Palmaz et al. |
| 2004/0148015 A1 | 7/2004 | Lye et al. | | 2005/0074479 A1 | 4/2005 | Weber et al. |
| 2004/0153138 A1 | 8/2004 | Murphy | | 2005/0074545 A1 | 4/2005 | Thomas |
| 2004/0157073 A1 | 8/2004 | Burrell et al. | | 2005/0077305 A1 | 4/2005 | Guevara |
| 2004/0158308 A1 | 8/2004 | Hogendijk et al. | | 2005/0079132 A1 | 4/2005 | Wang et al. |
| 2004/0158310 A1 | 8/2004 | Weber et al. | | 2005/0079199 A1 | 4/2005 | Heruth et al. |
| 2004/0167572 A1 | 8/2004 | Roth et al. | | 2005/0079356 A1 | 4/2005 | Rathenow et al. |
| 2004/0167612 A1 | 8/2004 | Grignani et al. | | 2005/0092615 A1 | 5/2005 | Birdsall et al. |
| 2004/0172124 A1 | 9/2004 | Vallana et al. | | 2005/0096731 A1 | 5/2005 | Looi et al. |
| 2004/0181252 A1 | 9/2004 | Boyle et al. | | 2005/0100577 A1 | 5/2005 | Parker et al. |
| 2004/0181275 A1 | 9/2004 | Noble et al. | | 2005/0100609 A1 | 5/2005 | Claude |
| 2004/0181276 A1 | 9/2004 | Brown et al. | | 2005/0102025 A1 | 5/2005 | Laroche et al. |

| | | | | | | |
|---|---|---|---|---|---|---|
| 2005/0106212 A1 | 5/2005 | Gertner et al. | | 2006/0014039 A1 | 1/2006 | Zhang et al. |
| 2005/0107869 A1 | 5/2005 | Sirhan et al. | | 2006/0015175 A1 | 1/2006 | Palmaz et al. |
| 2005/0107870 A1 | 5/2005 | Wang et al. | | 2006/0015361 A1 | 1/2006 | Sattler et al. |
| 2005/0113936 A1 | 5/2005 | Brustad et al. | | 2006/0020742 A1 | 1/2006 | Au et al. |
| 2005/0119723 A1 | 6/2005 | Peacock | | 2006/0025848 A1 | 2/2006 | Weber et al. |
| 2005/0129727 A1 | 6/2005 | Weber et al. | | 2006/0035026 A1 | 2/2006 | Atanassoska et al. |
| 2005/0131509 A1 | 6/2005 | Atanassoska et al. | | 2006/0036281 A1 | 2/2006 | Patterson et al. |
| 2005/0131521 A1 | 6/2005 | Marton | | 2006/0036311 A1 | 2/2006 | Nakayama et al. |
| 2005/0131522 A1 | 6/2005 | Stinson et al. | | 2006/0038027 A1 | 2/2006 | O'Connor et al. |
| 2005/0131527 A1 | 6/2005 | Pathak | | 2006/0040388 A1 | 2/2006 | Bromberg et al. |
| 2005/0131528 A1 | 6/2005 | Buscemi et al. | | 2006/0041182 A1 | 2/2006 | Forbes et al. |
| 2005/0136090 A1 | 6/2005 | Falotico et al. | | 2006/0051397 A1 | 3/2006 | Maier et al. |
| 2005/0137677 A1 | 6/2005 | Rush | | 2006/0052744 A1 | 3/2006 | Weber |
| 2005/0137679 A1 | 6/2005 | Changelian et al. | | 2006/0052863 A1 | 3/2006 | Harder et al. |
| 2005/0137684 A1 | 6/2005 | Changelian et al. | | 2006/0052864 A1 | 3/2006 | Harder et al. |
| 2005/0149169 A1 | 7/2005 | Wang et al. | | 2006/0058868 A1 | 3/2006 | Gale et al. |
| 2005/0149170 A1 | 7/2005 | Tassel et al. | | 2006/0062820 A1 | 3/2006 | Gertner et al. |
| 2005/0149175 A1 | 7/2005 | Hunter et al. | | 2006/0064160 A1 | 3/2006 | Gerold et al. |
| 2005/0149177 A1 | 7/2005 | Weber et al. | | 2006/0067908 A1 | 3/2006 | Ding |
| 2005/0159804 A1 | 7/2005 | Lad et al. | | 2006/0069427 A1 | 3/2006 | Savage et al. |
| 2005/0159805 A1 | 7/2005 | Weber et al. | | 2006/0075044 A1 | 4/2006 | Fox et al. |
| 2005/0159809 A1 | 7/2005 | Hezi-Yamit et al. | | 2006/0075092 A1 | 4/2006 | Kidokoro |
| 2005/0160600 A1 | 7/2005 | Bien et al. | | 2006/0085062 A1 | 4/2006 | Lee et al. |
| 2005/0163821 A1 | 7/2005 | Sung et al. | | 2006/0085065 A1 | 4/2006 | Krause et al. |
| 2005/0163954 A1 | 7/2005 | Shaw | | 2006/0088566 A1 | 4/2006 | Parsonage et al. |
| 2005/0165301 A1 | 7/2005 | Smith et al. | | 2006/0088567 A1 | 4/2006 | Warner et al. |
| 2005/0165468 A1 | 7/2005 | Marton | | 2006/0088653 A1 | 4/2006 | Chappa et al. |
| 2005/0165470 A1 | 7/2005 | Weber | | 2006/0088666 A1 | 4/2006 | Kobrin et al. |
| 2005/0169969 A1 | 8/2005 | Li et al. | | 2006/0100696 A1 | 5/2006 | Atanasoska et al. |
| 2005/0171595 A1 | 8/2005 | Feldman et al. | | 2006/0115512 A1 | 6/2006 | Peacock et al. |
| 2005/0177226 A1 | 8/2005 | Banik et al. | | 2006/0118236 A1 | 6/2006 | House et al. |
| 2005/0180919 A1 | 8/2005 | Tedeschi | | 2006/0121080 A1 | 6/2006 | Lye et al. |
| 2005/0182361 A1 | 8/2005 | Lennox | | 2006/0122694 A1 | 6/2006 | Stinson et al. |
| 2005/0182478 A1 | 8/2005 | Holman et al. | | 2006/0122697 A1 | 6/2006 | Shanley et al. |
| 2005/0186250 A1 | 8/2005 | Gertner et al. | | 2006/0124472 A1 | 6/2006 | Rokicki |
| 2005/0187605 A1 | 8/2005 | Greenhalgh et al. | | 2006/0127266 A1 | 6/2006 | Miura et al. |
| 2005/0187611 A1 | 8/2005 | Ding et al. | | 2006/0129215 A1 | 6/2006 | Helmus et al. |
| 2005/0192657 A1 | 9/2005 | Colen et al. | | 2006/0129222 A1 | 6/2006 | Stinson |
| 2005/0192662 A1 | 9/2005 | Ward | | 2006/0129225 A1 | 6/2006 | Kopia et al. |
| 2005/0192664 A1 | 9/2005 | Eisert | | 2006/0136048 A1 | 6/2006 | Pacetti et al. |
| 2005/0196424 A1 | 9/2005 | Chappa | | 2006/0141156 A1 | 6/2006 | Viel et al. |
| 2005/0208098 A1 | 9/2005 | Castro et al. | | 2006/0149352 A1 | 7/2006 | Schlun |
| 2005/0208100 A1 | 9/2005 | Weber et al. | | 2006/0153729 A1 | 7/2006 | Stinson et al. |
| 2005/0209680 A1 | 9/2005 | Gale et al. | | 2006/0155361 A1 | 7/2006 | Schomig et al. |
| 2005/0209681 A1 | 9/2005 | Curcio et al. | | 2006/0167543 A1 | 7/2006 | Bailey et al. |
| 2005/0211680 A1 | 9/2005 | Li et al. | | 2006/0177480 A1 | 8/2006 | Sung et al. |
| 2005/0214951 A1 | 9/2005 | Nahm et al. | | 2006/0178727 A1 | 8/2006 | Richter |
| 2005/0216074 A1 | 9/2005 | Sahatjian | | 2006/0184235 A1 | 8/2006 | Rivron et al. |
| 2005/0216075 A1 | 9/2005 | Wang et al. | | 2006/0193886 A1 | 8/2006 | Owens et al. |
| 2005/0220853 A1 | 10/2005 | Dao et al. | | 2006/0193887 A1 | 8/2006 | Owens et al. |
| 2005/0221072 A1 | 10/2005 | Dubrow et al. | | 2006/0193888 A1 | 8/2006 | Lye et al. |
| 2005/0222671 A1 | 10/2005 | Schaeffer et al. | | 2006/0193889 A1 | 8/2006 | Spradlin et al. |
| 2005/0228477 A1 | 10/2005 | Grainger et al. | | 2006/0193890 A1 | 8/2006 | Owens et al. |
| 2005/0228483 A1 | 10/2005 | Kaplan et al. | | 2006/0193892 A1 | 8/2006 | Furst et al. |
| 2005/0228491 A1 | 10/2005 | Snyder et al. | | 2006/0195142 A1 | 8/2006 | Shalaby |
| 2005/0232968 A1 | 10/2005 | Palmaz et al. | | 2006/0198869 A1 | 9/2006 | Furst et al. |
| 2005/0233965 A1 | 10/2005 | Schwartz et al. | | 2006/0199876 A1 | 9/2006 | Troczynski et al. |
| 2005/0234538 A1 | 10/2005 | Litvack et al. | | 2006/0200229 A1 | 9/2006 | Burgermeister et al. |
| 2005/0244459 A1 | 11/2005 | DeWitt et al. | | 2006/0200231 A1 | 9/2006 | O'Brien et al. |
| 2005/0251245 A1 | 11/2005 | Sieradzki et al. | | 2006/0200232 A1 | 9/2006 | Phaneuf et al. |
| 2005/0251249 A1 | 11/2005 | Sahatjian | | 2006/0200233 A1 | 9/2006 | Kujawski |
| 2005/0255707 A1 | 11/2005 | Hart et al. | | 2006/0204441 A1 | 9/2006 | Atala et al. |
| 2005/0261760 A1 | 11/2005 | Weber | | 2006/0204445 A1 | 9/2006 | Atala et al. |
| 2005/0266039 A1 | 12/2005 | Weber | | 2006/0210595 A1 | 9/2006 | Singhvi et al. |
| 2005/0266040 A1 | 12/2005 | Gerberding | | 2006/0212108 A1 | 9/2006 | Tittelbach |
| 2005/0266041 A1 | 12/2005 | Gerold et al. | | 2006/0222679 A1 | 10/2006 | Shanley et al. |
| 2005/0267561 A1 | 12/2005 | Jones et al. | | 2006/0222844 A1 | 10/2006 | Stinson |
| 2005/0271703 A1 | 12/2005 | Anderson et al. | | 2006/0224237 A1 | 10/2006 | Furst et al. |
| 2005/0271706 A1 | 12/2005 | Anderson et al. | | 2006/0229711 A1 | 10/2006 | Yan et al. |
| 2005/0276837 A1 | 12/2005 | Anderson et al. | | 2006/0229713 A1 | 10/2006 | Shanley et al. |
| 2005/0278016 A1 | 12/2005 | Welsh et al. | | 2006/0230476 A1 | 10/2006 | Atanasoska et al. |
| 2005/0278021 A1 | 12/2005 | Bates et al. | | 2006/0233941 A1 | 10/2006 | Olson |
| 2005/0281863 A1 | 12/2005 | Anderson et al. | | 2006/0241739 A1 | 10/2006 | Besselink et al. |
| 2005/0283224 A1 | 12/2005 | King | | 2006/0251701 A1 | 11/2006 | Lynn et al. |
| 2005/0283229 A1 | 12/2005 | Dugan et al. | | 2006/0259133 A1 | 11/2006 | Sowinski et al. |
| 2005/0287188 A1 | 12/2005 | Anderson et al. | | 2006/0264138 A1 | 11/2006 | Sowinski et al. |
| 2006/0002979 A1 | 1/2006 | Ashammakhi et al. | | 2006/0271156 A1 | 11/2006 | Ledergerber |
| 2006/0009839 A1 | 1/2006 | Tan | | 2006/0271168 A1 | 11/2006 | Kleine et al. |
| 2006/0013850 A1 | 1/2006 | Domb | | 2006/0271169 A1 | 11/2006 | Lye et al. |

| | | | | | | |
|---|---|---|---|---|---|---|
| 2006/0271192 A1 | 11/2006 | Olsen et al. | | 2007/0281073 A1 | 12/2007 | Gale et al. |
| 2006/0275554 A1 | 12/2006 | Zhao et al. | | 2007/0281117 A1 | 12/2007 | Kaplan et al. |
| 2006/0276877 A1 | 12/2006 | Owens et al. | | 2007/0282432 A1 | 12/2007 | Stinson et al. |
| 2006/0276878 A1 | 12/2006 | Owens et al. | | 2007/0299509 A1 | 12/2007 | Ding |
| 2006/0276879 A1 | 12/2006 | Lye et al. | | 2007/0299512 A1 | 12/2007 | Korzuschnik et al. |
| 2006/0276884 A1* | 12/2006 | Lye et al. ............ 623/1.39 | | 2008/0003251 A1 | 1/2008 | Zhou |
| 2006/0276885 A1 | 12/2006 | Lye et al. | | 2008/0003256 A1 | 1/2008 | Martens et al. |
| 2006/0280770 A1 | 12/2006 | Hossainy et al. | | 2008/0004691 A1 | 1/2008 | Weber et al. |
| 2006/0292388 A1 | 12/2006 | Palumbo et al. | | 2008/0031765 A1 | 2/2008 | Gerold et al. |
| 2007/0003589 A1 | 1/2007 | Astafieva et al. | | 2008/0033522 A1 | 2/2008 | Grewe et al. |
| 2007/0003596 A1 | 1/2007 | Tittelbach et al. | | 2008/0033530 A1 | 2/2008 | Zberg et al. |
| 2007/0020306 A1 | 1/2007 | Schultheiss | | 2008/0033531 A1 | 2/2008 | Barthel et al. |
| 2007/0027532 A1 | 2/2007 | Wang et al. | | 2008/0033533 A1 | 2/2008 | Borck |
| 2007/0032858 A1 | 2/2007 | Santos et al. | | 2008/0033536 A1 | 2/2008 | Wittchow |
| 2007/0032862 A1 | 2/2007 | Weber et al. | | 2008/0033537 A1 | 2/2008 | Tittelbach |
| 2007/0032864 A1 | 2/2007 | Furst et al. | | 2008/0033538 A1 | 2/2008 | Borck et al. |
| 2007/0034615 A1 | 2/2007 | Kleine | | 2008/0033539 A1 | 2/2008 | Sternberg et al. |
| 2007/0036905 A1 | 2/2007 | Kramer | | 2008/0033576 A1 | 2/2008 | Gerold et al. |
| 2007/0038176 A1 | 2/2007 | Weber et al. | | 2008/0038146 A1 | 2/2008 | Wachter et al. |
| 2007/0038289 A1 | 2/2007 | Nishide et al. | | 2008/0050413 A1 | 2/2008 | Horvers et al. |
| 2007/0038290 A1 | 2/2007 | Huang et al. | | 2008/0051335 A1 | 2/2008 | Kleiner et al. |
| 2007/0045252 A1 | 3/2007 | Kleine et al. | | 2008/0051866 A1 | 2/2008 | Chen et al. |
| 2007/0048350 A1 | 3/2007 | Falotico et al. | | 2008/0051872 A1 | 2/2008 | Borck |
| 2007/0050007 A1 | 3/2007 | Kondyurin et al. | | 2008/0051881 A1 | 2/2008 | Feng et al. |
| 2007/0050009 A1 | 3/2007 | Flanagan | | 2008/0057105 A1 | 3/2008 | Atanasoska et al. |
| 2007/0052497 A1 | 3/2007 | Tada | | 2008/0058919 A1 | 3/2008 | Kramer-Brown et al. |
| 2007/0055349 A1 | 3/2007 | Santos et al. | | 2008/0058921 A1 | 3/2008 | Lindquist |
| 2007/0055354 A1 | 3/2007 | Santos et al. | | 2008/0058923 A1 | 3/2008 | Bertsch et al. |
| 2007/0055364 A1 | 3/2007 | Hossainy et al. | | 2008/0069854 A1 | 3/2008 | Xiao et al. |
| 2007/0059435 A1 | 3/2007 | Santos et al. | | 2008/0069858 A1 | 3/2008 | Weber |
| 2007/0065418 A1 | 3/2007 | Vallana et al. | | 2008/0071348 A1 | 3/2008 | Boismier et al. |
| 2007/0073385 A1 | 3/2007 | Schaeffer et al. | | 2008/0071349 A1 | 3/2008 | Atanasoska et al. |
| 2007/0073390 A1 | 3/2007 | Lee | | 2008/0071350 A1* | 3/2008 | Stinson ............ 623/1.15 |
| 2007/0077163 A1 | 4/2007 | Furst et al. | | 2008/0071351 A1 | 3/2008 | Flanagan et al. |
| 2007/0104753 A1 | 5/2007 | Flanagan | | 2008/0071352 A1 | 3/2008 | Weber et al. |
| 2007/0106347 A1 | 5/2007 | Lin | | 2008/0071353 A1 | 3/2008 | Weber et al. |
| 2007/0106363 A1 | 5/2007 | Weber | | 2008/0071355 A1 | 3/2008 | Weber et al. |
| 2007/0123973 A1 | 5/2007 | Roth et al. | | 2008/0071357 A1 | 3/2008 | Girton et al. |
| 2007/0129789 A1 | 6/2007 | Cottone, Jr. et al. | | 2008/0071358 A1 | 3/2008 | Weber et al. |
| 2007/0129792 A1 | 6/2007 | Picart et al. | | 2008/0082162 A1 | 4/2008 | Boismier et al. |
| 2007/0134288 A1 | 6/2007 | Parsonage et al. | | 2008/0086199 A1 | 4/2008 | Dave et al. |
| 2007/0135908 A1 | 6/2007 | Zhao | | 2008/0086201 A1 | 4/2008 | Weber et al. |
| 2007/0141106 A1 | 6/2007 | Bonutti et al. | | 2008/0090097 A1 | 4/2008 | Shaw et al. |
| 2007/0142897 A1 | 6/2007 | Consigny et al. | | 2008/0097577 A1 | 4/2008 | Atanasoska et al. |
| 2007/0142899 A1 | 6/2007 | Lootz et al. | | 2008/0103589 A1 | 5/2008 | Cheng et al. |
| 2007/0148251 A1 | 6/2007 | Hossainy et al. | | 2008/0103594 A1 | 5/2008 | Loffler et al. |
| 2007/0151093 A1 | 7/2007 | Curcio et al. | | 2008/0107890 A1 | 5/2008 | Bureau et al. |
| 2007/0156231 A1 | 7/2007 | Weber | | 2008/0109072 A1 | 5/2008 | Girton |
| 2007/0156248 A1 | 7/2007 | Marco et al. | | 2008/0124373 A1 | 5/2008 | Xiao et al. |
| 2007/0160641 A1 | 7/2007 | Jang | | 2008/0131479 A1 | 6/2008 | Weber et al. |
| 2007/0168016 A1 | 7/2007 | Gronemeyer et al. | | 2008/0140172 A1 | 6/2008 | Carpenter et al. |
| 2007/0173923 A1 | 7/2007 | Savage et al. | | 2008/0140186 A1 | 6/2008 | Grignani et al. |
| 2007/0178129 A1 | 8/2007 | Flanagan | | 2008/0145400 A1 | 6/2008 | Weber et al. |
| 2007/0181433 A1 | 8/2007 | Birdsall et al. | | 2008/0147175 A1 | 6/2008 | Krivoruchko et al. |
| 2007/0184083 A1 | 8/2007 | Coughlin | | 2008/0147177 A1 | 6/2008 | Scheuermann et al. |
| 2007/0190104 A1 | 8/2007 | Kamath et al. | | 2008/0152929 A1 | 6/2008 | Zhao |
| 2007/0191923 A1 | 8/2007 | Weber | | 2008/0160166 A1 | 7/2008 | Rypacek et al. |
| 2007/0191928 A1 | 8/2007 | Rolando et al. | | 2008/0160259 A1 | 7/2008 | Nielson et al. |
| 2007/0191931 A1 | 8/2007 | Weber | | 2008/0161906 A1 | 7/2008 | Atanasoska et al. |
| 2007/0191943 A1 | 8/2007 | Shrivastava et al. | | 2008/0171929 A1 | 7/2008 | Katims |
| 2007/0197980 A1 | 8/2007 | Barry et al. | | 2008/0175885 A1 | 7/2008 | Asgari |
| 2007/0202466 A1 | 8/2007 | Schwarz et al. | | 2008/0177378 A1 | 7/2008 | Asgari |
| 2007/0207186 A1 | 9/2007 | Scanlon et al. | | 2008/0183269 A2 | 7/2008 | Kaplan et al. |
| 2007/0208412 A1 | 9/2007 | Elmaleh | | 2008/0183277 A1 | 7/2008 | Atanasoska et al. |
| 2007/0219626 A1 | 9/2007 | Rolando et al. | | 2008/0183278 A1 | 7/2008 | Atanasoska et al. |
| 2007/0224116 A1 | 9/2007 | Chandrasekaran et al. | | 2008/0188927 A1 | 8/2008 | Rohde et al. |
| 2007/0224244 A1 | 9/2007 | Weber et al. | | 2008/0195170 A1 | 8/2008 | Asgari |
| 2007/0225799 A1 | 9/2007 | Doty | | 2008/0195189 A1 | 8/2008 | Asgari |
| 2007/0244541 A1 | 10/2007 | Schulman | | 2008/0195198 A1 | 8/2008 | Asgari |
| 2007/0244569 A1 | 10/2007 | Weber et al. | | 2008/0208308 A1 | 8/2008 | Allen et al. |
| 2007/0250155 A1 | 10/2007 | Simpson | | 2008/0208313 A1 | 8/2008 | Yu et al. |
| 2007/0250156 A1 | 10/2007 | Palmaz | | 2008/0208352 A1 | 8/2008 | Krivoruchko et al. |
| 2007/0250158 A1 | 10/2007 | Krivoruchko et al. | | 2008/0213377 A1 | 9/2008 | Bhatia et al. |
| 2007/0255388 A1 | 11/2007 | Rudakov et al. | | 2008/0215129 A1 | 9/2008 | Venturelli et al. |
| 2007/0255392 A1 | 11/2007 | Johnson | | 2008/0215139 A1 | 9/2008 | McMorrow et al. |
| 2007/0264199 A1 | 11/2007 | Labhasetwar et al. | | 2008/0215140 A1 | 9/2008 | Borck et al. |
| 2007/0264303 A1 | 11/2007 | Atanasoska et al. | | 2008/0241218 A1 | 10/2008 | McMorrow et al. |
| 2007/0270940 A1 | 11/2007 | Doty | | 2008/0243113 A1 | 10/2008 | Shastri et al. |
| 2007/0270942 A1 | 11/2007 | Thomas | | 2008/0243230 A1 | 10/2008 | Lootz et al. |

| | | |
|---|---|---|
| 2008/0243231 A1 | 10/2008 | Flanagan et al. |
| 2008/0243234 A1 | 10/2008 | Wilcox |
| 2008/0243240 A1 | 10/2008 | Doty et al. |
| 2008/0243242 A1 | 10/2008 | Kappelt et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255509 A1 | 10/2008 | Wang |
| 2008/0262589 A1 | 10/2008 | Nagura |
| 2008/0269872 A1 | 10/2008 | Lootz et al. |
| 2008/0288048 A1 | 11/2008 | Rolando et al. |
| 2008/0290467 A1 | 11/2008 | Shue |
| 2008/0294236 A1 | 11/2008 | Anand et al. |
| 2008/0294246 A1 | 11/2008 | Scheuermann |
| 2008/0306584 A1 | 12/2008 | Kramer-Brown |
| 2009/0005862 A1 | 1/2009 | Nakatani et al. |
| 2009/0012599 A1 | 1/2009 | Broome et al. |
| 2009/0018639 A1 | 1/2009 | Kuehling |
| 2009/0018647 A1 | 1/2009 | Benco et al. |
| 2009/0018648 A1 | 1/2009 | Wittchow |
| 2009/0024199 A1 | 1/2009 | Birdsall et al. |
| 2009/0024209 A1 | 1/2009 | Ozdil et al. |
| 2009/0024210 A1 | 1/2009 | Klocke et al. |
| 2009/0024211 A1 | 1/2009 | Wittchow |
| 2009/0028785 A1 | 1/2009 | Clarke |
| 2009/0030494 A1 | 1/2009 | Stefanadis et al. |
| 2009/0030500 A1 | 1/2009 | Weber et al. |
| 2009/0030504 A1 | 1/2009 | Weber et al. |
| 2009/0030506 A1 | 1/2009 | Klocke et al. |
| 2009/0030507 A1 | 1/2009 | Klocke et al. |
| 2009/0035351 A1 | 2/2009 | Berglund et al. |
| 2009/0043330 A1 | 2/2009 | To |
| 2009/0043374 A1 | 2/2009 | Nakano |
| 2009/0043380 A1 | 2/2009 | Blaha et al. |
| 2009/0048660 A1 | 2/2009 | Adden |
| 2009/0062905 A1 | 3/2009 | Moore, Jr. et al. |
| 2009/0069884 A1 | 3/2009 | Mueller |
| 2009/0076588 A1 | 3/2009 | Weber |
| 2009/0076596 A1 | 3/2009 | Adden et al. |
| 2009/0081293 A1 | 3/2009 | Murase et al. |
| 2009/0081450 A1 | 3/2009 | Ascher et al. |
| 2009/0088831 A1 | 4/2009 | Goto |
| 2009/0088834 A1 | 4/2009 | Wang |
| 2009/0093871 A1 | 4/2009 | Rea et al. |
| 2009/0095715 A1 | 4/2009 | Sabaria |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118819 A1 | 5/2009 | Merz et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0124956 A1 | 5/2009 | Swetlin et al. |
| 2009/0131540 A1 | 5/2009 | Hiromoto et al. |
| 2009/0143855 A1 | 6/2009 | Weber et al. |
| 2009/0149942 A1 | 6/2009 | Edelman et al. |
| 2009/0157165 A1 | 6/2009 | Miller et al. |
| 2009/0157172 A1 | 6/2009 | Kokate et al. |
| 2009/0164002 A1 | 6/2009 | Becher et al. |
| 2009/0171452 A1 | 7/2009 | Yamamoto et al. |
| 2009/0177273 A1 | 7/2009 | Piveteau et al. |
| 2009/0182290 A1 | 7/2009 | Harder et al. |
| 2009/0182337 A1 | 7/2009 | Stopek et al. |
| 2009/0182425 A1 | 7/2009 | Duda et al. |
| 2009/0192571 A1 | 7/2009 | Stett et al. |
| 2009/0192594 A1 | 7/2009 | Borck |
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0198320 A1 | 8/2009 | Mueller et al. |
| 2009/0202610 A1 | 8/2009 | Wilson |
| 2009/0204203 A1 | 8/2009 | Allen et al. |
| 2009/0208428 A1 | 8/2009 | Hill et al. |
| 2009/0208555 A1 | 8/2009 | Kuttler et al. |
| 2009/0214373 A1 | 8/2009 | Stinson et al. |
| 2009/0220612 A1 | 9/2009 | Perera |
| 2009/0228037 A1 | 9/2009 | Rego |
| 2009/0240323 A1 | 9/2009 | Wilcox |
| 2009/0254171 A1 | 10/2009 | Heikkila |
| 2009/0259300 A1 | 10/2009 | Dorogy, Jr. et al. |
| 2009/0270979 A1 | 10/2009 | Adden |
| 2009/0274737 A1 | 11/2009 | Borck |
| 2009/0281613 A1 | 11/2009 | Atanasoska et al. |
| 2009/0287301 A1 | 11/2009 | Weber |
| 2009/0287302 A1 | 11/2009 | Thomas et al. |
| 2009/0306584 A1 | 12/2009 | Schmidtlein et al. |
| 2009/0306756 A1 | 12/2009 | Cho et al. |
| 2009/0306765 A1 | 12/2009 | Weber |
| 2009/0306766 A1 | 12/2009 | McDermott et al. |
| 2009/0311300 A1 | 12/2009 | Wittchow |
| 2009/0312807 A1 | 12/2009 | Boudreault et al. |
| 2009/0319035 A1 | 12/2009 | Terry |
| 2009/0324684 A1 | 12/2009 | Atanasoska et al. |
| 2009/0326638 A1 | 12/2009 | Atanasoska et al. |
| 2010/0008970 A1 | 1/2010 | O'Brien et al. |
| 2010/0010621 A1 | 1/2010 | Klocke |
| 2010/0010640 A1 | 1/2010 | Gerold et al. |
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1 | 2/2010 | Radhakrishnan et al. |
| 2010/0034899 A1 | 2/2010 | Harder et al. |
| 2010/0042205 A1 | 2/2010 | Atanasoska et al. |
| 2010/0042206 A1 | 2/2010 | Yadav et al. |
| 2010/0047312 A1 | 2/2010 | Wittchow |
| 2010/0047324 A1 | 2/2010 | Fritz et al. |
| 2010/0049146 A1 | 2/2010 | Nielsen et al. |
| 2010/0049296 A1 | 2/2010 | Sarasam et al. |
| 2010/0049299 A1 | 2/2010 | Popowski et al. |
| 2010/0049300 A1 | 2/2010 | Harder |
| 2010/0055151 A1 | 3/2010 | Flanagan |
| 2010/0057188 A1 | 3/2010 | Weber |
| 2010/0057197 A1 | 3/2010 | Weber et al. |
| 2010/0075162 A1 | 3/2010 | Yang et al. |
| 2010/0076544 A1 | 3/2010 | Hoffmann et al. |
| 2010/0076556 A1 | 3/2010 | Tomantschger et al. |
| 2010/0081735 A1 | 4/2010 | Mao et al. |
| 2010/0082092 A1 | 4/2010 | Gerold |
| 2010/0087910 A1 | 4/2010 | Weber |
| 2010/0087911 A1 | 4/2010 | Mueller |
| 2010/0087914 A1 | 4/2010 | Bayer et al. |
| 2010/0087915 A1 | 4/2010 | Bayer et al. |
| 2010/0087916 A1 | 4/2010 | Bayer et al. |
| 2010/0092535 A1 | 4/2010 | Cook et al. |
| 2010/0106243 A1 | 4/2010 | Wittchow |
| 2010/0119576 A1 | 5/2010 | Harder et al. |
| 2010/0119581 A1 | 5/2010 | Gratz et al. |
| 2010/0121432 A1 | 5/2010 | Klocke et al. |
| 2010/0125325 A1 | 5/2010 | Allen et al. |
| 2010/0125328 A1 | 5/2010 | Flanagan |
| 2010/0131050 A1 | 5/2010 | Zhao |
| 2010/0131052 A1 | 5/2010 | Kappelt et al. |
| 2010/0161031 A1 | 6/2010 | Papirov et al. |
| 2010/0217370 A1 | 8/2010 | Scheuermann et al. |

FOREIGN PATENT DOCUMENTS

| | | |
|---|---|---|
| AU | 2003 203 722 | 11/2003 |
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 038236 | 2/2008 |
| EP | 0 006 544 | 6/1979 |
| EP | 0 337 035 | 10/1989 |
| EP | 0 923 389 | 7/1998 |
| EP | 0 923 912 | 6/1999 |

| | | |
|---|---|---|
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 260 214 | 11/2002 |
| EP | 1 270 023 | 1/2003 |
| EP | 1 273 314 | 1/2003 |
| EP | 1 370 306 | 12/2003 |
| EP | 1 389 471 | 2/2004 |
| EP | 1 419 793 | 5/2004 |
| EP | 0 951 877 | 6/2004 |
| EP | 0 875 218 | 2/2005 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |
| RU | 2 218 242 | 12/2003 |
| WO | WO 93/04118 | 3/1993 |
| WO | WO 97/11724 | 4/1997 |
| WO | 98/29025 | 7/1998 |
| WO | WO 98/48851 | 11/1998 |
| WO | 99/33410 | 7/1999 |
| WO | WO 99/47077 | 9/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | 00/54704 | 9/2000 |
| WO | WO 00/66190 | 11/2000 |
| WO | WO 01/49338 | 7/2001 |
| WO | WO 01/78906 | 10/2001 |
| WO | 01/80920 | 11/2001 |
| WO | 01/87371 | 11/2001 |
| WO | WO 02/45764 | 6/2002 |
| WO | WO 02/47739 | 6/2002 |
| WO | WO 02/53202 | 7/2002 |
| WO | 03/002243 | 1/2003 |
| WO | WO 03/013396 | 2/2003 |
| WO | 03/035134 | 5/2003 |
| WO | WO 03/035131 | 5/2003 |
| WO | WO 03/035278 | 5/2003 |
| WO | WO 03/063733 | 8/2003 |
| WO | WO 03/094990 | 11/2003 |
| WO | 2004/029313 | 4/2004 |
| WO | 2004/043292 | 5/2004 |
| WO | WO 2004/093643 | 11/2004 |
| WO | 2005/025449 | 3/2005 |
| WO | WO 2005/065576 | 7/2005 |
| WO | 2005/079335 | 9/2005 |
| WO | WO 2005/110395 | 11/2005 |
| WO | WO 2005/118019 | 12/2005 |
| WO | WO 2006/008739 | 1/2006 |
| WO | WO 2006/060033 | 6/2006 |
| WO | WO 2006/060534 | 6/2006 |
| WO | WO 2006/065356 | 6/2006 |
| WO | 2006/077154 | 7/2006 |
| WO | 2006/080381 | 8/2006 |
| WO | 2006/097503 | 9/2006 |
| WO | 2006/104644 | 10/2006 |
| WO | WO 2006/108065 | 10/2006 |
| WO | WO 2007/005806 | 1/2007 |
| WO | 2007/013102 | 2/2007 |
| WO | WO 2007/018931 | 2/2007 |
| WO | 2007/035791 | 3/2007 |
| WO | WO 2007/024552 | 3/2007 |
| WO | 2007/0079363 | 7/2007 |
| WO | 2007/079636 | 7/2007 |
| WO | WO 2007/082147 | 9/2007 |
| WO | 2007/139668 | 12/2007 |
| WO | 08/034048 | 3/2008 |
| WO | 08/034066 | 3/2008 |
| WO | 2008/003450 | 3/2008 |
| WO | WO 2008/062414 | 5/2008 |
| WO | 2008/092436 | 8/2008 |
| WO | 2008/106271 | 9/2008 |
| WO | 2008/118606 | 10/2008 |
| WO | WO 2008/117315 | 10/2008 |

OTHER PUBLICATIONS

Ferrando, "Review of Corrosion and Corrosion Control of Magnesium Alloys and Composites," *J. Mater. Eng.*, 1989, 11:299-313.
Gray and Luan, "Protective coatings on magnesium and its alloys—a critical review," *J. Alloys Compounds*, 2002, 336:88-113.
Park et al., "Microstructural change and precipitation hardening in melt-spun Mg-X-Ca alloys," *Science and Technology of Advanced Materials*, 2001, 2:73-78.
Straumal et al., "Vacuum arc deposition of protective layers on glass and polymer substrates," *Thin Solid Films*, 2001, 383:224-226.
Wang et al., "Nonlinear optical properties of thin iron films grown on MgO (100) by pulsed laser deposition," *Thin Solid Films*, 2005, 471:86-90.
U.S. Appl. No. 10/849,742, Chen et al.
U.S. Appl. No. 60/826,002, filed Sep. 18, 2006, Girton et al.
U.S. Appl. No. 60/862,318, filed Oct. 20, 2006, Atanasoska et al.
U.S. Appl. No. 60/845,136, filed Sep. 15, 2006, Weber et al.
"Galvanic cell" printout from wikipedia, 2 pgs, printed Oct. 28, 2005.
"Galvanic corrosion", http://www.corrosion-doctors.org/Aircrafi/galvdefi.htm, 3 pgs., printed Oct. 28, 2005.
"Galvanic series" printout from Wikipedia, p. 1 of 2, printed Oct. 28, 2005.
"Best of the ACC Scientific Session 2002," *Rev. Cardiovasc. Med.*, 2002, 3(2):85-104.
"Corrosion Theory and Corrosion Protection," *EM 1110-2-3400*, 1995, 8 pages.
Aghion et al., "Newly Developed Magnesium Alloys for Powertrain Applications," *JOM*, 2003, p. 30.
Andión et al., "Corrosion behaviour at the interface of steel bars embedded in cement slurries. Effect of phenol polymer coatings,"*Corrosion Science*, 2002, 44:2805-2816.
Antipov et al., "Polyelectrolyte Multilayer Capsule Permeability Control " *Colloids and Surfaces A: Physiochem. Eng. Aspects*, 2002, 198-200, 535-541.
Antipov et al., "Polyelectrolyte Multilayer Capsules as Vehicles with Tunable Permeability," *Advances in Colloid and Interface Science*, 2004, 111:49-61.
Arts et al., "Polyphenols and disease risk in epidemiologic studies," *Am. J. Clin. Nutr.*, 2005, 81:317S-325S.
Artyukhin et al., "Layer-by-Layer Electrostatic Self-Assembly of Polyelectrolyte Nanoshells on Individual Carbon Nanotube Templates," *Langmuir*, 2004, 20:1442-1448.
Bach et al., "Corrosion, Protection and Repassivation After the Deformation of Magnesium Alloys Coated With a Protective Magnesium Fluoride Layer," *JOM*, 2004, p. 343.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.
Baurschmidt et al., "The Electrochemical Aspects of the Thrombogenicity of a Material,"*J. Bioengineering*, 1977, 1:261-278.
Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.
Berry et al., "Functionalisation of magnetic nanoparticles for applications in biomedicine," *J. Phys. D: Appl. Phys.*, 2003, 36:R198-R206.
Bolz et al., "Effect of smooth, porous and fractal surface structure on the properties of an interface," *J. Materials Science: Materials in Medicine*, 1995, 6:844-848.
Brandau et al., "Nanoporous Ceramic Coatings for Synthesis of Radioactive Implants " *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al., "Inhibition of the corrosion of steel in 1 M HC1 by eugenol derivatives," *Applied Surface Science*, 2005, 246:199-206.

Changwen et al., "Polyoxometalate-based organic-inorganic hybrid materials"; http://www.solgel.com/articles/oct01/changwen.asp, Retrieved from the Internet on Nov. 1, 2004 (17 pages).

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

International Search Report/Written Opinion in PCT/US05/16600 mailed May 4, 2006, 15 pages.

International Preliminary Report on Patentability in PCT/US05/16600 mailed Nov. 30, 2006, 7 pages.

International Preliminary Report on Patentability in PCT/US07/78476 mailed Mar. 26, 2009, 7 pages.

Authorized Officer Simin Baharlou, International Search Report/Written Opinion in PCT/US07/66568 mailed Oct. 8, 2007, 11 pages.

Authorized Officer Simin Baharlou, International Preliminary Report on Patentability in PCT/US07/66568 mailed Oct. 23, 2008, 10 pages.

International Search Report/Written Opinion in PCT/US07/78505 mailed Mar. 4, 2008, 10 pages.

International Preliminary Report on Patentability in PCT/US07/78505 mailed Mar. 26, 2009, 7 pages.

Authorized Officer Athina Nickitas-Etienne, International Search Report/Written Opinion in PCT/US07/78449, mailed Jan. 13, 2009, 24 pages.

Authorized Officer Athina Nickitas-Etienne, International Preliminary Report on Patentability in PCT/US07/78449 mailed Mar. 26, 2009, 9 pages.

Authorized Officer Simin Baharlou, International Search Report/Written Opinion in PCT/US07/75072 mailed Jan. 25, 2008, 21 pages.

Authorized Officer Simin Baharlou, International Preliminary Report on Patentability in PCT/US07/75072 mailed Feb. 12, 2009, 9 pages.

Véronique van Loon-Mégard, International Search Report/Written Opinion in PCT/US07/78429 mailed Mar. 28, 2008, 13 pages.

Véronique van Loon-Mégard International Preliminary Report on Patentability in PCT/US07/78429 mailed Apr. 2, 2009, 8 pages.

Melanie Geuer, International Search Report/Written Opinion in PCT/US07/78411 mailed Mar. 6, 2008, 12 pages.

Melanie Geuer, International Preliminary Report on Patentability in PCT/US07/78411 mailed Feb. 4, 2009, 8 pages.

Authorized Officer Elisabeth Reinecke, International Search Report/Written Opinion in PCT/US07/60137 mailed Jul. 27, 2007, 20 pages.

Melanie Geuer, International Preliminary Report on Patentability in PCT/US07/78412 mailed Apr. 2, 2009, 7 pages.

Authorized Officer Trudy Hinterwimmer, International Search Report/Written Opinion in PCT/US07/78412 mailed Mar. 3, 2008, 10 pages.

Authorized Officer Joëlle Gerber, International Search Report/Written Opinion in PCT/US07/78450 mailed Nov. 19, 2008, 17 pages.

Sierra Gonzalez, International Preliminary Report on Patentability in PCT/US07/78450 mailed Mar. 26, 2009, 7 pages.

Josephina Tschuck, International Search Report/Written Opinion in PCT/US07/73839 mailed Apr. 16, 2008, 17 pages.

Josephina Tschuck, International Preliminary Report on Patentability in PCT/US07/73839 mailed Apr. 2, 2009, 10 pages.

Authorized Officer Cecilia Giel-Barragán Ramos, International Search Report/Written Opinion in PCT/US07/79841 mailed Feb. 4, 2009, 21 pages.

Authorized Officer Athina Nickitas-Etienne, International Preliminary Report on Patentability in PCT/US07/79841 mailed Apr. 30, 2009, 7 pages.

Authorized Officer Joëlle Gerber, International Search Report/Written Opinion in PCT/US07/88888 mailed Jul. 13, 2009, 24 pages.

Authorized Officer Nora Lindner, International Preliminary Report on Patentability in PCT/US07/88888 mailed Jul. 30, 2009, 11 pages.

Authorized Officer Véronique van Loon-Mégard, International Search Report/Written Opinion in PCT/US08/75976 mailed Nov. 25, 2008, 20 pages.

Authorized Officer Trudy Hinterwimmer, International Search Report/Written Opinion in PCT/US09/49422 mailed Aug. 24, 2009, 10 pages.

Damiani et al., "Vasorelaxant effects on eugenol on rat thoracic aorta," *Vascular Pharmacol.*, 2003, 40:59-66.

Dexter, "Galvanic Corrosion," MAS Note, University of Delaware Sea Grant Marine Advisory Service, 2003.

Di Mario et al., "Moonlight: a controlled registry of an iridium-oxide coated stent with angiographic follow up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duygu, "Controlled Release Systems," http://www.biomed.metu.edu.tr/courses/term_papers/contr-rel-sys_duygu.htm (Dec. 30, 2005).

Eniola and Hammer, "Characterization of biodegradable drug delivery vehicles with the adhesive properties of leukocytes II: effect of degradation on targeting activity," *Biomaterials*, 2005, 26:661-670.

Farhat et al., "Corrosion Control Using Polyelectrolyte Multilayers," *Electrochemical and Solid State Letters*, 2002, 5(4):B13-B15.

Fischer et al., "Hydrogen in magnesium alloys and magnesium interfaces: preparation, electronic properties and interdiffusion," *J. Less Comm Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Frei, "On the Role of Vitamin C and Other Antioxidants in Atherogenesis and Vascular Dysfunction," *Proceedings—Society for Experimental Biology and Medicine*, 1999, 222:196-204.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Guo et al., "Multi-layer LB films of single-wall carbon nanotubes," *Physica B*, 2002, 323:235-236.

Guo et al., "Manipulation of single-wall carbon nanotubes into aligned molecular layers," *Chem. Phys. Lett.*, 2002, 362:314-318.

Gurib-Fakim, "Medicinal plants: Traditions of yesterday and drugs of tomorrow" *Molecular Aspects of Medicine*, 2006, 27:1-93.

Haferkamp et al., "Magnesium-Base-Alloys as Implant-Material Steps to the Production of Thin Components," *Magnesium*, 2000, 159-164.

Hau et al., "Surface-Chemistry Technology for Microfluidics," *J. Micromech. Microeng.*, 2003, 13:272-278.

Huang et al., "A Review on Polymer Nanofibers by Electro-spinning and their Applications in Nanocomposites," *Composites Science & Technology*, 2003, 63:2223-2253.

Heublein et al., "Biocorrosion of magnesium alloys: a new principle in cardiovascular implant technology?" *Heart*, 2003, 89:651-656.

Heublein et al., "Bio-corrosion—a new principle for temporary cardiovascular implants?" *European Heart Journal, Journal of the European Society of Cardiology*, 2000, vol. 21, p. 286, Abstract No. P1605.

Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.

Heublein et al., "Local Tissue Engineering by Biocorrosion Vision or Reality?" *The American Journal of Cardiology, TCT Abstracts/Poster*, Oct. 16, 2000.

Ito et al., "Antioxidant action of eugenol compounds; role of metal ion in the inhibition of lipid peroxidation," *Food Chem. Toxicol.*, 2005, 43:461-466.

Ivanova and Ivanov, "Mechanisms of the extracellular antioxidant defend." *Experimental Pathology and Parasitology*, 2000, 4:49-59.

Jiang, "A review of wet impregnation—An alternative method for the fabrication of high performance and nano-structured electrodes of solid oxide fuel cells," *Materials Science and Engineering A*, 2006, 418:199-210.

Kean and Davies, "Cathodic Protection," 7 pages, 1981; http://www.npl.co.uk/upload/pdf/cathodic_protection.pdf.

Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.

Kim et al., "Effect of Anti-Oxidant (Carvedilol and Probucol) Loaded Stents in a Porcine Coronary Restenosis Model," *Circ. J.*, 2005, 69:101-106.

Kong et al., "Polyelectrolyte-functionalized multiwalled carbon nanotubes: preparation, characterization and layer-by-layer self assembly," *Polymer*, 2005, 46:2472-2485.

Kumar et al., "Polyanhydrides: an overview," *Advanced Drug Delivery Reviews*, 2002, 54:889-910.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_4 2[Mo_{132}O_{372}(CH_3COO)_{30}(H_2O)_{72}]$," *Chem. Mater.*, 2000, 12:2829-2831.

Lambert et al., "Inhibition of carcinogenesis by polyphenols: evidence from laboratory investigations " *Am. J. Clin. Nutr.*, 2005, 81:284S-291S.

Lee et al., "Retentive and compressive strengths of modified zinc oxide-eugenol cements," *J. Dentistry*, 2000, 28:69-75.

Liao et al., "Fabrication of porous biodegradable polymer scaffolds using a solvent mergin/particulate leaching method," *J. Biomed. Mater. Res.*, 2002, 59(4):676-681.

Lin et al., "Micropatterning proteins and cells on polylactic acid and poly(lactide-*co*-glycolide)," *Biomaterials*, 2005, 26:3655-3662.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Maier et al., "High concentrations of magnesium modulate vascular endothelial cell behaviour in vitro," *Biochim. Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Matsuoka et al., "Hyperthermia Using Magnetitc Cationic Liposomes for Hamster Osteosarcoma," *BioMagnetic Research and Technology*, 2004, 2:3-8.

Medical Device Daily, "Conor Cites Positive 12-month Results for Its CoStar Stent", May 2005 (1 page).

Middleton and Tipton, "Synthetic Biodegradable Polymers as Medical Devices," http://www.devicelink.com/mnb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):1-6.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Mohanty et al. "Evaluation of soft tissue response to a poly[urethane urea]," *Biomaterials*, 1992, 13(10):651-656.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81:277S-283S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Nilsson et al., "Development of a dosage method for electrochemical treatment of tumours: a simplified mathematical model," *Bioelectrochemistry and Bioenergetics*, 1998, 47:11-18.

Ou et al., "Protective effects of eugenol against oxidized LDL-induced cytotoxicity and adhesion molecule expression in endothelial cells," *Food Chem. Toxicol.*, 2006, 44:1485-1495.

Peuster et al., "Long-term biocompatibility of a corrodible peripheral iron stent in the porcine of descending aorta," *Biomaterials*, 2006, 27:4955-4962.

Peuster et al., "A novel approach to temporary stenting: degradable cardiovascular stents produced from corrodible metal-results 6-18 months after implantation into New Zealand white rabbits," *Heart*, 2001, 86(5).

Prasse et al., "Electric Anisotropy of Carbon Nanofibre/Epoxy Resin Composites Due to Electric Field Induced Alignment," *Composites Science and Technology*, 2003, 63:1835-1841.

Ratnam et al., "Role of antioxidants in prophylaxis and therapy: A pharmaceutical persepective," *J. Controlled Release*, 2006, 113:189-207.

Remskar et al., "Self-Assembly of Subnanometer-Diameter Single-Wall $MoS_2$ Nanotubes," *Science*, 2001, 292:479-481.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rutledge et al., "Electrostatic Spinning and Properties of Ultrafine Fibers," *National Textile Center Annual Report*, Nov. 2001, M01-D22, pp 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-338.

Schetky, "Shape Memory Alloys," *Encyclopedia of Chemical Technology* (3rd ed.), 1962, John Wiley & Sons, 20:726.

Shaw, "Corrosion Resistance of Magnesium Alloys," *ASM Handbook vol. 13A: Corrosion: Fundamentals, Testing, and Protection*, 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electrospinning: the Electrically Forced Jet and Instabilities," *Polymer*, 2001, 42:9955-9967.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Suslick et al., "The Photochemistry of Chromium, Manganese, and Iron Porphyrin Complexes," *J. Chem.*, 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Vermette et al., "Immobilized Liposome Layers for Drug Delivery Applications," *J. Controlled Release*, 2002, 80:179-195.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Wallerath et al., "A blend of polyphenols explains the stimulatory effect of red wine on human endothelial NO synthase," *Nitric Oxide*, 2005, 12(2):97-104.

Wan et al., "Influence of Plasma Immersion Ion Implantation on Corrosion Properties of Magnesium," South Jiaotong University, Chengdu, 2005.

Wang et al., "Characterisation of Severely Deformed Austenitic Stainless Steel Wire," *Materials Science and Technology*, 2005, 21:1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271:407-415.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Williamson et al., "Bioavailability and bioefficacy of polyphenols in humans. II. Review of 93 intervention studies," *Am. J. Clin. Nutr.*, 2005, 81:243S-255S.

Witte et al., "In vitro and in vivo corrosion measurements of magnesium alloys," *Biomaterials*, 2006, 27:1013-1018.

Yamaguchi et al., "Mg2Si Coating Technology on Magnesium Alloys to Improve Corrosion and Wear Resistance", *JOM*, 2004, p. 343.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta Mat.*, 2000, 42:1089-1094.

Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Zeta Potential—An Introduction in 30 Minutes, Technical Note; http://www.nbtc.cornell.edu/facilities/downloads/Zeta%20potential%20-%20An%20introduction%20in%2030%20minutes.pdf, Retrieved from the Internet on May 9, 2005 (6 pages).

Zhang et al., "Natural Polyelectrolyte Films Based on Layer-by-Layer Deposition of Collagen and Hyaluronic Acid," *Biomaterials*, 2005, 26:3353-3361.

Zhang et al., "Improving multilayer films endurance by photoinduced interaction between Dawson-type polyoxometalate and diazo resin," *Materials Chemistry and Physics*, 2005, 90:57-52.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zhou et al., "Drug-loaded, Magnetic, hollow silica nanocomposites for nanomedicine," *Nanomedicine: Nanotechnology, Biology and Medicine*, 2005, 1:233-237.

Zucchi et al., "Influence of a silane treatment on the corrosion resistance of a WE43 magnesium alloy," *Surface Coatings Technol.*, 2006, 200:4136-4143.

Aaltonen, "Atomic Layer Deposition of Noble Metal Thin Films," *University of Helsinki*, Apr. 8, 2005, pp. 1-71.

Albion Research Notes, Newsletter, Oct. 1994, 3(4): 1-4.

Anand et al., "Ion-exchange resins: carrying drug delivery forward," *DDT*, 2001, 6: 905-914.

Anderson et al., "A new conductive polymer as a replacement for chrome conversion coatings," *2003 Aerospace Coatings Removal and Coatings Conference*, May 20-22, 2003, Colorado Springs, CO, 7 pages.

Ashtari et al. "An efficient method for recovery of target ssDNA based on amino-modified silica-coated magnetic nanoparticles" *Talanta 67*. (2005). 548-554.

Atta, "Electrochemical synthesis, characterization and some properties of a polymer derived from thioflavm S.," *European Polymer Journal*, 2005, 41: 3018-3025.

Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.

Authorized officer Athina Nickitas-Etienne, International Preliminary Report on Patentability in PCT/US08/86639 mailed Jun. 24, 2010, 2 pages.

International Search Report/Written Opinion in PCT/US2008/86639 mailed Feb. 23, 2010, 8 pages.

International Search Report/Written Opinion in PCT/US2009/43326 mailed Aug. 6, 2009, 9 pages.

Babapulle and Eisenberg, "Coatred stents for their prevention of restenosis: Part II," *Circulation*, 2021, 106: 2849-2866.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly (aniline-co-2-anisdine) films on stainless steel," *Progress in Organic Coatings*, 2005, 54:63-72.

Bernkop-Schnurch, "Chitosan and its derivatives: potential excipients for peroral peptide delivery systems," *International J. of Pharmaceutics*, 2000, 194: 1-13.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bosiers et al., "Absorbable Metal stent for CLI in Infrapopliteal lesions: 1 year results," *CX 2005 Global Endovascular Forum*, Apr. 2005, pp. 1-23.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.

Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.

Chang et al., "Templated sythesis of Gold-iron Alloy nanoparticles using pulsed laser deposition," *Nanotechnology*, vol. 17, 2006, pp. 5131-5135.

Chen et al., "Laser Cladding of Mg20A18o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}^{3-}$ (x=0,3,6,12)," *Synthetic Metals*, 2002, 129: 53-59.

Cho et al., "Gold-coated iron nanoparticles: a novel magnetic resonance agent for $T1$ and $T2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Di Mario et al., "Drug-eluting bioabsorbable 17(6): 391-395 magnesium stent," *J. Interventional Cardiol.*, 2004, 17(6): 391-395.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer therapeutics," *Nature Reviews/Drug Discovery*, 2003, 2: 347-360.

Eggebrecht et al., "Novel Magnetic Resonance-Compatible Coronary Stent: The Absorbable Magnesium-Alloy Stent," *Circulation*, 2005, 112: 303-304.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

European Examiner Marie-France Weiss, International Preliminary report on Patentability received in PCT/US2007/078417, mailed Mar. 26, 2009, 8 pages.

European Examiner Melanie Geuer, International Preliminary Report on Patentability, received in PCT/US2007/078407, mailed Mar. 26, 2009, 6 pages.

European Search Report from EP 10159664.1, mailed Jun. 4, 2010, 3 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Feng et al., "Sonochemical preparation of photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion-Fatigue Performance of Magnesium Alloys," *International Journal of Modern Physics B*, vol. 17, Nos. 8 & 9, 2003, pp. 1601-1607.

Fischer et al., "Determination of in-vivo corrosion rates of degradable implants by SR-microtomography," date unknown, pp. 1-2.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer Ezrt, "Quantitative material analysis by dual energy computed tomography for industrial NDT applications," 2009, 1 pg.

Fraunhofer IIS-Poster (German), "Prinzip der hochauflösenden Comptuertomographie," 2009, 1 page.

Gabrielli, Claude. "Use and Applications of Electrochemical Impedance Techniques," *Solartron Analytical*, 1997, 1-102.

Garner et al., "Polypyrrole-heparin composites as stimulus-responsive substrates for endothelial cell growth," *J. Biomed. Mater. Res.*, 1999, 44: 121-129.

Gettleman et al., "Measurement of in vivo corrosion rates in baboons, and correlation with in vitro tests," Journal of Dental Research, 1980, 59: 689-707.

Gettleman et al., "Materials Science: Measurement of in vivo Corrosion Rates in Baboons, and Correlation with in vitro Tests," *Journal of Dental Research*, 1980, vol. 59, pp. 689-707.

Griffiths et al., "Future devices: bioabsorbable stents," *Br. J. Cardiol. (Acute & Interventional Cardiology)*, 2004, 11: AIC80-AIC84.

Grube, "Bioabsorbable Stents-The Boston Scientific & REVA Technology," *EuroPCR 2009*, 2009, pp. 1-27.

Gu et al., "In vitro Corrosion and biocompatibility of binary magnesium alloys," *Biomaterials*, vol. 30, 2009, pp. 484-498.

Gupta et al., "Nanometer spaced electrodes using selective area layer deposition," *Applied Physics Letters*, vol. 90, 2007, pp. 1-4.

Haenzi et al., "Design strategy for microalloyed ultra-ductile Mg alloys," 2009, *Phil. Mag. Letters*, 89(6): 377-390.

Haenzi et al., "Design strategy for new biodegradable Mg-Y-Zn alloys for medical applications," *Int. J. Mat. Res.*, 2009, 100: 1127-1136.

Haenzi et al., "On the biodegradation performance of an Mg-Y-Re alloy with various surface conditions in simulated body fluid," *Acto Biomat.*, 2009, 5: 162-171.

Hamu et al., "Influence of Si, Ca and Ag addition on corrosion behavior of new wrought Mg-Zn alloys," 2006, 22(10): 1213-1218.

Hänzi et al., "Design strategy for microalloyed ultra-ductile magnesium alloys," *Philosophical Magazine letters*, vol. 89, No. 6, Jun. 2009, pp. 377-390.

Hänzi et al., "Design strategy for new biodegradable Mg-Y-Zn alloys for medical applications," *Int. J. Mat. Res.*, vol. 100, 2009, pp. 1127-1136.

Hänzi et al., "On the biodegradation performance of an Mg-Y-Re alloy with various surface conditions in simulated body fluid," *Acta Biomaterialia*, vol. 5, 2009, pp. 162-171.

Hague et al. "Bioabsorption Qualities of Chitosan-absorbable Vascular Templates," *Current Surgery*, 2001, 58(1):77-80.

Heismann et al., "Density and atomic number measurements with spectral x-ray attenuation method," *Journal of Applied Physics*, vol. 94, No. 3, Aug. 1, 2003, pp. 2073-2079.

Hermawan et al., "Developments in metallic biodegradable stents," *Acta Biomaterialia*, 2010, 6:1693-1697.

Hermawan et al., "Degradable metallic biomaterials: Design and development of Fe-Mn alloys for stents," *Wiley InterScience: Article*, Apr. 19, 2008, pp. 1-12.

Hermawan et al., "Degradation Behaviour of Metallic Biomaterials for Degradable Stents," *Advanced Materials Research*, 2007, 15-17:113-118.

Hermawan et al., "Development of Degradable Fe-35Mn Alloy for Biomedical Application," *Advanced Material Research*, 2007, 15-17:107-112.

Hermawan et al., "Fe-Mn Alloys for Metallic Biodegradable Stents: Degradation and Cell Viability Studies," *Acta Biomaterialia*, Manuscript, Mar. 27, 2009, pp. 1-30.

Hermawan, et al., "Iron-Manganese: new class of metallic degradable biomaterials prepared by powder metallurgy," *Powder Metallurgy*, 2008, 51(1):38-45.

Hildebrandt et al., "Prevention of surface encrustation of urological implants by coating with inhibitors," *Biomaterials*, 2001, 22:503-507.

Holclajtner-Antunovic et al., "Study of some polyoxometallates of Keggin's type as potention antitumour agents," *Jugoslov Med. Biohem.*, 2004, 23: 25-30.

Hourng et al., Influence of multisteps thermal control in metal powder injection moulding process, *Powder Metallurgy*, 2008, 51: 84-89.

Hutten, A. et al. "Ferromagnetic FeCo nanoparticles for biotechnology". (2005) *Journal of Magnetism and Magnetic Materials* 293:93-101.

Iakovou et al., "Incidence, Predictors, and Outcome of Thrombosis Successful Implantation of Drug-Eluting Stents," *JAMA*, 2005, 293(17): 2126-2130.

Ignat et al., "Magnesium alloys (WE43 and ZE41) characterization for laser applications," *Applied Surface Science*, 2004, 233:382-391.

Iida et al. "Surface modification of of λFe2O3 nanoparticles with aminopropylsilyl groups and interparticle linkage with a,w-Dicarboxylic Acids". *Electrochimica Acta*. 2005. 855-859.

Imgrund, "Evaluation of metal injection moulding (MIM) and extrusion as processing technology for biodegradable stents. A 208143: Final report for phase I MIM of Fe and Fe-Si powders and sample characterisation," Aug. 15, 2008, *Fraunhofer Institut Fertigungstechnik Material forschung*, 18 pages.

Integran, "Biodegradable Nanometallic Intracoronary Stents," May 12, 2009, 1 page.

Integran, "Biodegradable Nanometallic Intracoronary Stents," Proposal, May 12, 2009, 1 page.

International Preliminary Report on Patentability received in PCT/US2007/078479, mailed Mar. 26, 2009, 8 pages.

International Search Report/Written Opinion in PCT/US09/046750 mailed Jul. 20, 2010, 14 pages.

International Search Report and Written Opinion received in PCT/US2007/078417, mailed Jan. 22, 2009, 18 pages.

International Search Report and Written Opinion received in PCT/US2007/078479, mailed Dec. 30, 2008, 12 pages.

International Search Report from PCT/US 03/20215, mailed Nov. 11, 2003, 4 pages.

International Search Report/Written Opinion in PCT/US2007/078407, mailed Mar. 26, 2008, 10 pages.

Jabara et al., "Bioabsorbable Stents: The Future is Near," *Cardiac Interventions Today*, Jun./Jul. 2009, pp. 50-53.

Jabara, "Poly-anhydride based on salicylic acid and adipic acid anhydride," Glimpse into the future: bioabsorbable stents-aimint to restore vascular integrity, *Euro PCR09*, 2009, pp. 1-34.

James A. Plambeck, "Electrolytic Processes of Nonmetals," *Chemical Sciences*, 1995, 2 pages.

Jiang et al., "Corrosion protection of polypyrrole electrodeposited on AZ91 magnesium alloys in alkaline solutions," *Synthetic Materials*, 2003, 139: 335-339.

Jiang et al., "Effect of $TiB_2$ particulate on partial remelting behavior of Mg-11A1-0.5Zn matrix composite," *Materials Science and Engineering A*, 2004, 381: 223-229.

Kaesel et al., "Approach to Control the Corrosion of Magnesium by Alloying," *Magnesium: Proceedings of the 6th International Conference Magnesium Alloys and Their Applications*, 2004, pp. 534-539.

Kainer, "Magnesium alloys and technology," Wiley VCH, 2003, 119 pages.

Kaya et al., "Microstructure and Corrosion Resistance of Alloys of the Mg-Zn-Ag System," *Metal Science and Heat Treatment*, 2006, 48(11-12): 524-530.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kokubo et al., "How useful is SBF in predicting in vivo bone bioactivity?" *Biomaterials*, 2006, 27:2907-2915.

LaFont, "Arterial Remodeling Technologies: Bioresorbable Stents," *Euro PCR09*, 2009, pp. 1-28.

Lee, J. et al. "Simple synthesis of mesoporous carbon with magnetic nano particles embedded in carbon rods". (2005) Carbon 43:2536-2543.

Lee, Sang-Yup et al. "Surface modification of magnetic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liu et al., "Characterizations of polypyrrole (PPy) nano-tubules made by templated ac electropolymerization," *European Polymer Journal*, 2005, 41: 2117-2121.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maendl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, 2007, 28:1689-1710.

Mansfeld, Florian. "Analysis and Interpretation of EIS Data for Metals and Alloys," *Solartron Analytical*,1999, 1-77.

Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.

Markman, "Absorbable Coronary stents," *The Lancet*, Jun. 2, 2007, 369:1839-1840.

Massaro et al., "Comparative Investigation implants. Part 1: chemical composition," *Journal of Materials Science: Materials in Medicine*, vol. 13, 2002, pp. 535-548.

Meng Han, "Laser nitriding of metals: Influences of the ambient pressure and the pulse duration," 2001, Dissertation, Georg-Aug.-Universität Göttingen, 134 pages.

Methods in Cell Biology (*Cell Death*), vol. 46, p. 163.

Miao et al., "Porous Calcium Phosphate Ceramics prepared by coating polyurethane foams with Calcium phosphate cements," *Materials Letters*, vol. 58, 2004, pp. 397-402.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niinisto, "Atomic Layer deposition: A key technology for the controlled growth of oxide thin films for advanced applications," *Proc. Estonian Acad. Sci. Phys. Math.*, 2003, 52(3):266-276.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.*

Ormiston et al., "Bioabsorbable Coronary Stents", *Circulation Cardiovasc Intervent*, vol. 2, 2009, pp. 255-260.*

Ouerd et al., "Reactivity of Titanium in Physiolgoical Medium—I. Electrochemical Characterization of the Metal/Protein Interface," *Journal of the Electrochemical Society*, vol. 154, No. 10, 2007, pp. 593-601.*

Oyane et al., "Preparation and assessment of revised simulated body fluids," 2003, *Wiley Periodicals*, Inc., 2003,*

Paliwoda-Porebska et al., "On the development of polypyrrole coatings with self-healing properties for iron corrosion protection," *Corrosion Science*, 2005, 47: 3216-3233.*

Peeters et al., "Preliminary Results after Application of Absorbable Metal Stents in Patients with Critical Limb Ischemia," *J. Endovasc Ther*, 2005, 12:1-5.*

Peeters, et al., "Preliminary Data on Absorbable Metal Stents," *MEET 2006*, Jun. 2006, pp. 1-30.*

Peuster et al., "Are resorbable implants about to become a reality," *Cardiol Young*, 2006, 16:107-116.*

Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.*

Purushothaman et al. "Reducing Mass-Transport Limitations by Application of Special Pulsed Current Modes". *Journal of the Electrochemical Society* 152 (4), 2005, J33-J39.*

Qasem et al., "Kinetics of paclitaxel 2'-N-methylpyridinium mesylate decomposition", *AAPS PharmSciTech*, 2003 4(2), Article21, 8 pages.*

Quinard et al., "Development of metal/polymer mixtures for micro powder injection Moulding" *10th ESAFORM Conference on Material Forming*, 2007, pp. 933-939.*

Qureshi et al., "The emerging role of iron, zinc, copper, magnesium and selenium and oxidative stress in health and diseases," *Biogenic Amines*, vol. 19, No. 2, 2005, pp. 147-169.*

Raman et al., "Laser assisted modification of surface microstructure for localised corrosion resistance of magnesium alloys," *Surface Engineering*, 2007, 23(2): 107-111.*

Reece et al., "Metal transport studies on inherently conducting polymer membranes containing cyclodextrin dopants," *Journal of Membrane Science*, 2005, 249: 9-20.*

Ren et al., "Variations of dose and electrode spacing for rat breast cancer electrochemical treatment," *Bioelectromagnetics*, 2001, 22(3):205-211.*

Rettig et al., "Composition of corrosion layers on a magnesium rare-earth alloy in simulated body fluids," *Journal of Biomedical Materials Research Part A*, Oct. 18, 2006, pp. 359-369.*

Rettig et al., "Corrosion resistance studies on grain-boundary etched drug-eluting stents", *J. Mater Sci: Mater Med.*, 2007, vol. 18, pp. 1377-1387.*

Rettig et al., "Time-dependent electrochemical characterization of the corrosion of a magnesium rare-earth alloy in simulated body fluids", *Journal of Biomedical Materials Research Part A*, 2007, 167-175.*

Rinkevich et al., "Regeneration of Amputated Avian Bone by a Coral Skeletal Implany," *Biol. Bull.*, vol. 197, Aug. 1999, pp. 11-13.*

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Schauer et al., "Protection of iron against corrosion with polyaniline primers," *Progress in Organic Coatings*, 1998, 33: 20-27.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pages 671-673.

Secheresse et al., "$(Mo_2 O_2 X_2)_{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity-Introduction & Objectives," *Euro PCR09*, May 18, 2009, pp. 1-4.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shieh et al. "Aqueous dispersions of magnetite nanoparticles with NH3 surfaces for magnetic manipulations of biomolecules and MRI contrast agents" *Biomaterials*, 2005 26: 7183-7191.

Sieber, et al., "Investigations on the passivity of iron in borate and phosphate buffers, pH 8.4," *Corrosion Science*, vol. 48, 2006, pp. 3472-3488.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science.* 2004. 75:1-68.

Soto et al., "Amorphous magnesium nitride films produced by reactive pulsed lasar deposition," Journal of Non-Crystalline Solids, 2004, 342: 65-69.

Stoner et al., "The mechanism of low frequency a.c. Electrochemical Disinfection," *Bioelectrochemistry and Bioenergetics*, 1982, 9:229-243.

Su et al., "Photoacoustic imaging of coronary artery stents," *Optics Express*, vol. 17, No. 22, Oct. 26, 2009, pp. 1-8.

Sun et al., "Fabrication of a multilayer film electrode containing porphyrin and its application as a potentiometric sensor of iodide ion," *Talanta*, 1998, 46: 15-21.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Virtanen et al., "Electrochemical Behavior of Fe in Phosphate Solutions Studied by *In Situ* X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, pp. 147-171.

Volkova, "Effect of Deformation and Heat Treatment on the Structure and Properties of Magnesium Alloys of the Mg-Zn-Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009, pp. 1-16.

Wan et al., "Preparation and characterization of porous conducting poly(DL-lactide) composite membrances," *Journal of Membrane Science*, 2005, 246: 193-201.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

Weiss et al., "Pyrrole derivatives for electrochemical coating of metallic medical devices," *J. Polymer Science, Part A: Polymer Chemistry*, 2004, 42: 1658-1667.

White and Slade, "Polymer electrodes doped with heteropolymetallates and their use within solid-state supercapacitors," *Synthetic Metals*, 2003, 139: 123-131.

Wilcox, "Biodegradable Technology: Medtronic Biodegradable Stent Program," *Euro PCR09*, pp. 1-25.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol.28, 2007, pp. 2163-2174.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6:1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg-MnZn alloy for bone implant application," *Journal of Biomedical Materials Research Part A*, Jun. 4, 2007, pp. 703-711.

Ye et al., "In situ synthesis of AlN particles in Mg-A1 alloy by $Mg_3$-$N_2$ addition," *Materials Letters*, 2004, 58: 2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zheng, "Symposium on Biodegradable/Biocorroded metallic materials," Nov. 24, 2009, pp. 1-74.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

International Search Report and Written Opinion from PCT/US09/043591, mailed Jun. 30, 2010, 10 pages.

International Search Report from PCT/US07/005671, mailed Jun. 2, 2008, 10 pages.

Ma et al., "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper," *Colloids and Surfaces A: Physiochem. Eng. Aspects*, 2006, 273: 16-23.

International Preliminary Report on Patentability from PCT/US08/75976 dated Mar. 25, 2010, mailed Nov. 25, 2008, 8 pages.

Macias et al., "Electrospun mesoporous Materials, 2005, 86: 1-13 metal oxide fibers," *Microporous and Mesoporous Materials*, 2005, 86: 1-13.

Viswanathamurthi et al., "Preparation and morphology of niobuim oxide fibres by electrospinning," *Chemical Physics Letters*, 2003, 374: 79-84.

International Preliminary Report on Patentability from PCT/US09/043326 mailed Nov. 18, 2010, 7 pages.

Authorized Officer Jasmine Messemanne, International Preliminary Report on Patentability from PCT/US09/051965 mailed Feb. 10, 2011, 8 pages.

US 6,533,715, 03/2003, Hossainy et al. (withdrawn)

* cited by examiner

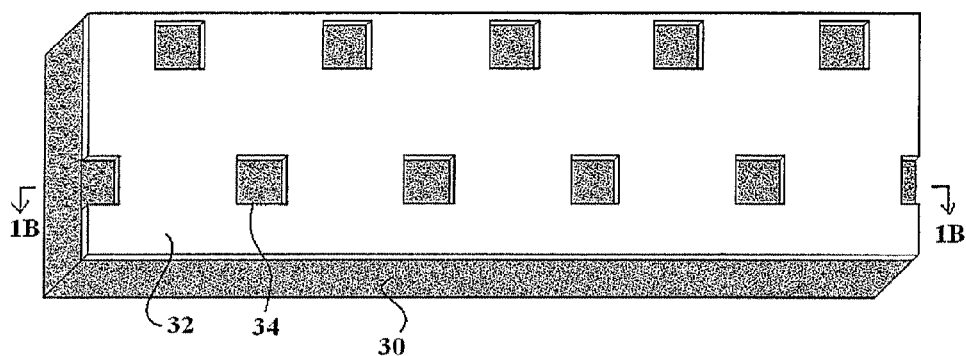
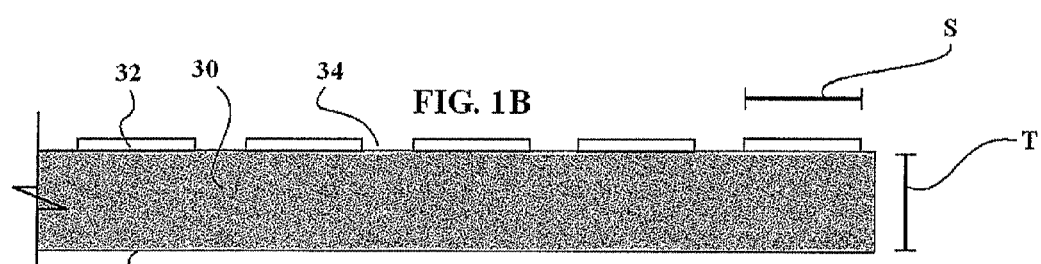
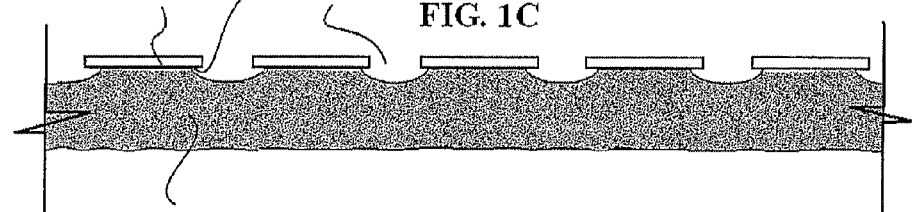
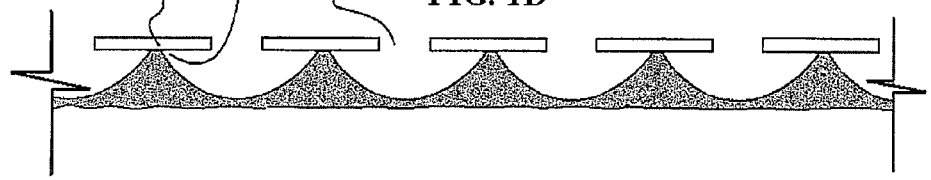

FIG. 3A
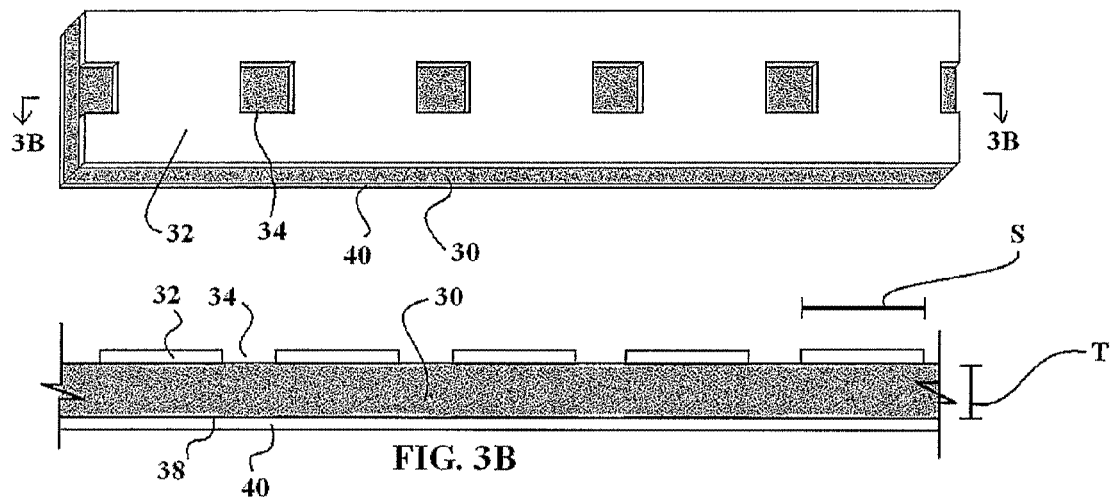
FIG. 3B
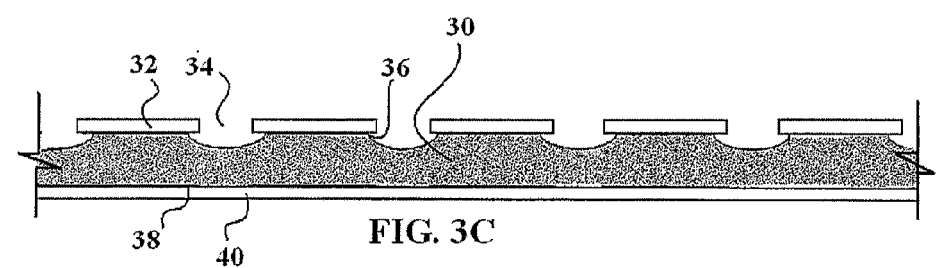
FIG. 3C
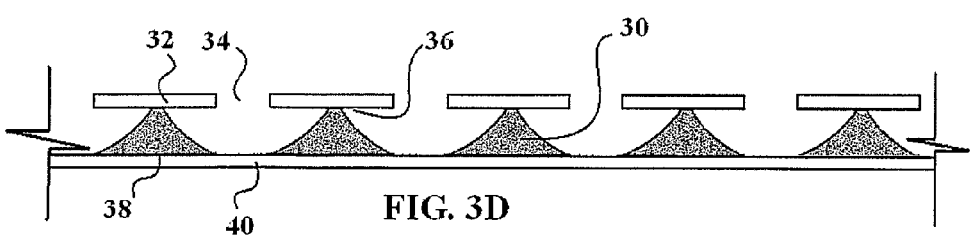
FIG. 3D

FIG. 4A
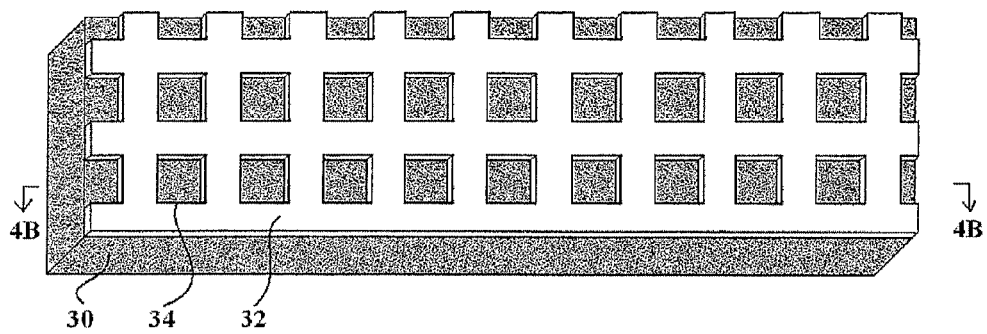
FIG. 4B
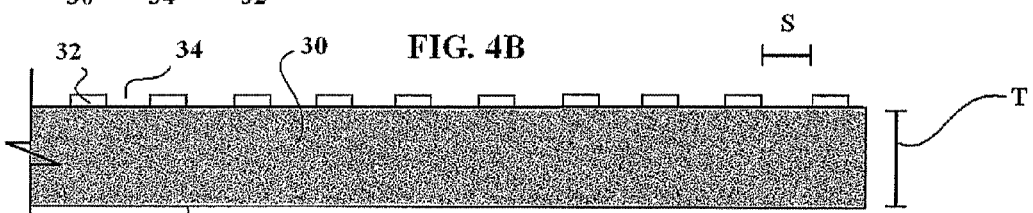
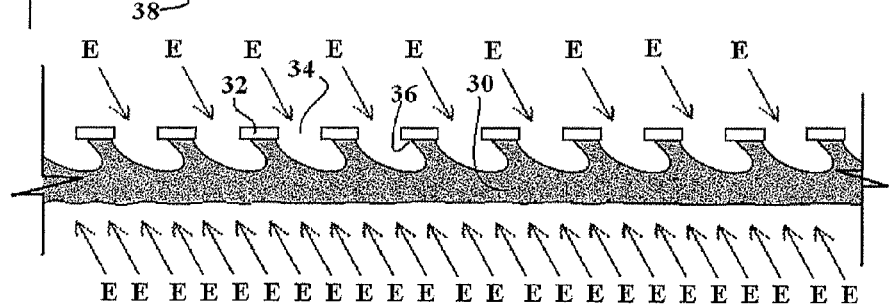
FIG. 4C
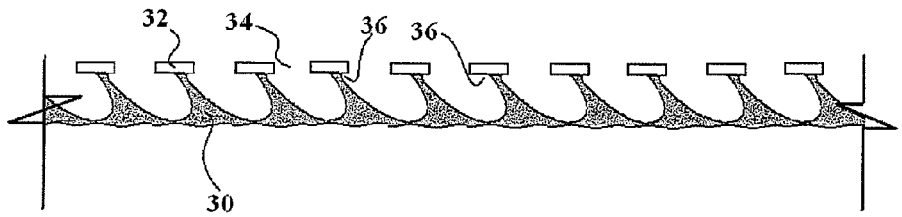
FIG. 4D

BIOERODIBLE ENDOPROSTHESIS

TECHNICAL FIELD

This invention relates to bioerodible endoprostheses.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

It is sometimes desirable for an implanted endoprosthesis to erode over time within the passageway. For example, a fully erodible endoprosthesis does not remain as a permanent object in the body, which may help the passageway recover to its natural condition. Erodible endoprostheses can be formed from, e.g., a polymeric material, such as polylactic acid, or from a metallic material, such as magnesium, iron or an alloy thereof.

SUMMARY

There is described an endoprosthesis that includes a plurality of struts defining a flow passage. At least one strut includes (a) a body comprising a bioerodible material and having a thickness and (b) a coating overlying the body. The coating includes a plurality of regions that allow physiological fluids to contact a plurality of corresponding areas of the underlying body when the endoprosthesis is implanted in a physiological environment. The plurality of regions are sized and arranged so that the contacted areas of the body erode substantially through the body in the thickness direction while the coating remains on the body when the endoprosthesis is implanted in the physiological environment.

The body can include bioerodible material that erodes isotropically and/or anisotropically. The rate of erosion of the body in the thickness direction multiplied by the thickness of the body can be less than a rate of erosion of the body along an interface between the body and the coating multiplied by the distance between adjacent regions. In some embodiments, the rate of erosion of the body in the thickness direction multiplied by the thickness of the body can be less than a rate of erosion of the body along an interface between the body and the coating multiplied by ½ of the distance between adjacent regions. For example, the plurality of regions can be arranged such that the distance between adjacent regions is equal to at least the thickness of the body (e.g., at least twice the thickness of the body).

The bioerodible material of the body can have a first electric potential and the coating has a second electric potential different from the first electric potential so that the body and the coating form a galvanic couple when the endoprosthesis is implanted in a physiological environment. In some embodiments, the first electric potential can be less than the second electrode potential so that the body acts as an anode and the coating acts as a cathode when the endoprosthesis is implanted in a physiological environment. For example, the body can include a bioerodible metal selected from the group consisting of magnesium, iron, zinc, and alloys thereof and the coating can include a metal selected from the group consisting of platinum, iridium, and alloys thereof. In other embodiments, the first electric potential can be greater than the second electrode potential so that the body acts as a cathode and the coating acts as an anode when the endoprosthesis is implanted within a physiological environment.

The bioerodible material of the body can be a bioerodible metal and/or a bioerodible polymer. For example, the body can include a bioerodible metal selected from magnesium, iron, zinc, and alloys thereof and/or a bioerodible polymer selected from polyglutamic acid, poly(ethylene oxide), polycaprolactam, poly(lactic-co-glycolic acid), polysaccharides, and combinations thereof.

The coating can surround or partially surround the circumference of the body. The coating can include a bioerodible material having a slower erosion rate than the bioerodible material of the body.

The regions of the coating can include voids, pores, and/or can have a higher erosion rate than the remainder of the coating in a physiological environment.

The endoprosthesis, in some embodiments, can be a stent.

The details of one or more embodiments are set forth in the accompanying drawings and the description below. Other features, objects, and advantages will be apparent from the description and drawings, and from the claims.

DESCRIPTION OF DRAWINGS

FIGS. 1A-1D depict a first embodiment of an endoprosthesis strut.

FIGS. 3A-3D depict a third embodiment of an endoprosthesis strut.

FIGS. 4A-4D depict a third embodiment of an endoprosthesis strut.

Like reference symbols in the various drawings indicate like elements.

DETAILED DESCRIPTION

Figure 2A:
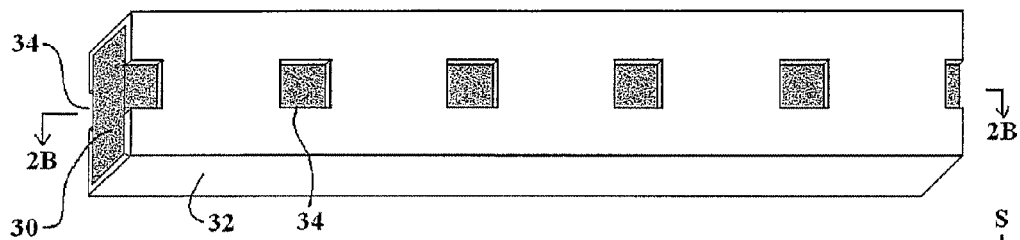
FIGS. 2A-2D depict a second embodiment of an endoprosthesis strut.

FIGS. 1A-1D, 2A-2D, 3A-3D, and 4A-4D depict different of an endoprosthesis strut having a body 30 that includes a bioerodible material and a coating 32 overlying at least a portion of the body 30. The coating 32 includes a plurality of regions 34 that expose a plurality of corresponding areas of the underlying body 30 to a physiological environment when the endoprosthesis is implanted within a physiological environment. As shown, the regions are simply voids in the coating. In other embodiments, the regions 34 can be porous regions and/or regions designed to erode prior to the remainder of the coating 32. The regions 34 are sized and arranged so that the exposed areas of the body erode substantially through the body in the thickness direction before the coating 32 separates from the body 30. The spacing of the regions can account for an undercutting of the coating during the erosion of the body of the endoprosthesis, namely the erosion of the bioerodible body along the interface between the body and the coating. For example, the coating can separate from the body 30 due to this erosion of the body 30 along the interface between the body 30 and the coating 32. If the regions are spaced too closely, this undercutting can result in a premature separation of the coating from the body.

The arrangement of regions, particularly the spacing between adjacent regions, is determined, in part, based on the thickness of the body and the erosion characteristics of the body 30 (e.g., whether the body 30 erodes isotropically or anisotropically). For a body 30 that erodes isotropically (i.e., homogeneously in all directions), the spacing S between adjacent regions can be at least equal to the thickness T of the body. For example, as shown in FIGS. 1C, 1D, 2C, 2D, 3C, and 3D, a body 30 that erodes isotropically can produce undercuts 36 beneath the edges of the regions 34 of the coating 32. For embodiments where the coating 32 is only on one side of the body 30, such as shown in FIGS. 1A-1D, a thickness T can be less than or equal to the spacing S between adjacent regions 34 to ensure that the body erodes substantially through the thickness T before the coating 32 separates from the body 30. In some embodiments, the body can be formed of a single bioerodible material having consistent erosion properties. In other embodiments, the body can be a composite of a plurality of bioerodible materials and can have varying erosion properties. The size and arrangement of the regions in the coating can depend on the overall erosion properties of the body.

As shown in FIGS. 1C and 1D, an uncoated opposite side 38 of the body 30 can erode in a substantially uniform manner across its surface, and at substantially the same rate as the body erodes inward in the thickness direction from the exposed areas of the regions 34. Having a thickness T that is less than the spacing S can ensure that the body 30 erodes substantially through the thickness, from both sides of the body, before adjacent undercuts from adjacent regions 34 erode into each other. In some embodiments, however, the placement of the endoprosthesis within a physiological environment can alter the rate of erosion of particular portions and/or sides of the endoprosthesis. For example, a side of an isotropic body 30 placed against a vessel wall may erode at a slower or faster rate than a portion of the body 30 positioned adjacent to flowing blood, depending on the characteristics of the material(s) of the body 30. The pH of the physiological environment can alter the erosion rate of some bioerodible materials and the erosion of various bioerodible materials can alter the pH of the surrounding fluids and/or tissues. The endoprosthesis can be designed so that the contacted areas of the body erode substantially through the body in the thickness direction while the coating remains on the body even with these variations to the erosion rate of the body.

Figure 2B:
Figure 2C:
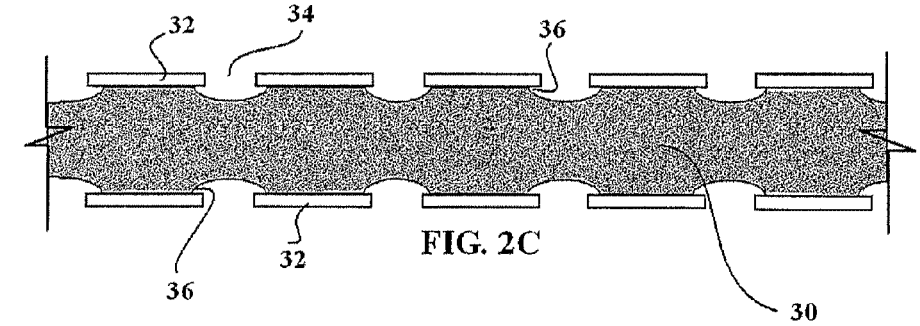

The body 30 can also include coatings on selected portions of the surface of the body (e.g., on more than one side). In some embodiments, the coating 32 can surround the entire circumference of the body 30. In other embodiments, the coating can extend along the length of the body 30 in selected portions around the circumference of the body 30. For example, as shown in FIGS. 3A-3C, the body can have coatings on opposite sides of the body 30, but have adjacent sides of the body remain exposed. The coatings on portions (or sides) of the body can have uniform or non-uniform patterns of regions. For example, as shown in FIGS. 2A-2B, a coating 32 can have identical patterns on opposite sides of the body and have adjacent sides without the presence of any regions. As shown, the regions of the opposite sides are aligned. In other embodiments, the regions can be offset. In some embodiments, opposite sides can have completely different arrangements of regions, different sizes of regions, and/or different spacing of regions. Although the body 30 is shown as having a rectangular cross-sectional shape, the body can have other cross-sectional shapes (e.g., circular or polygonal) and can have a non-constant cross-sectional shapes, thicknesses, and/or widths.

Figure 2D:
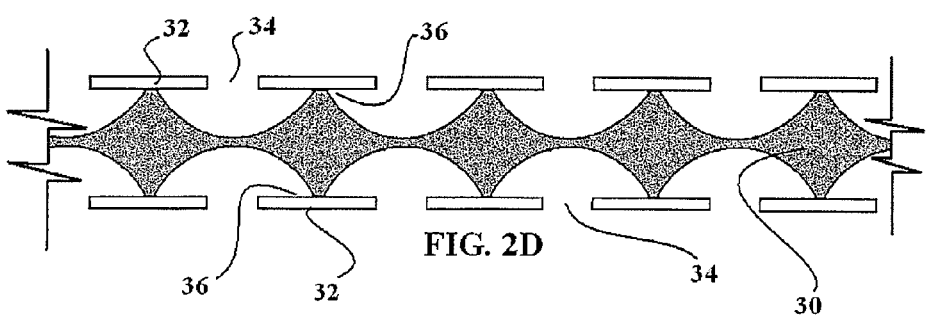

An isotropically eroding body 30 having identical and aligned patterns of regions on opposite sides of the body 30, as shown in FIGS. 2A-2D, can have a thickness T of less than or equal to the spacing S between adjacent regions 34. As shown in FIG. 2D, the regions 34 of opposite sides of the body 30 allow for erosions paths through the thickness of the body 30 that meet at the approximate center of the body 30, which provides an erosion path through the thickness of the body 30 prior to the separation of the coating 32 from the body 30 along the interface between the body 30 and the coating 32. A body 30 having different patterns of regions 34 on opposite sides of body 30 can allow for different maximum thicknesses depending on an amount of time required for erosion paths on opposite sides to intersect (if at all). If erosion paths do not intersect, for example, if body 30 has a region-free coating 40 on the opposite side 38 of the body 30 as shown in FIGS. 3A-3D, the thickness T of the body can be less than or equal to half of the spacing S between adjacent regions. As shown in FIG. 3D, the body 30 can erode through its thickness T prior to the separation of the coating 32 from the body 30. For example, iron and magnesium erode isotropically.

A body 30 that erodes anisotropically can allow for different arrangements of regions in the coating 32. The arrangement, however, must account for the different rates of erosion of the body in each direction. For example, as shown in FIGS. 4A-4D, an endoprosthesis having a body 30 that erodes anisotropically can allow for a closer spacing of adjacent regions 34 if the body 30 erodes at a faster rate in the thickness direction than in directions parallel with the coating. FIGS. 4C and 4D depict a preferred erosion direction E that results in a faster erosion rate in the thickness direction. In other embodiments, the preferred erosion direction E can be parallel to the thickness direction. In embodiments having a non-coated opposite underside 38 of the body as shown in FIGS. 4A-4D, the thickness T of the body can be less than or equal to the minimum spacing between the plurality of regions multiplied by the average rate of erosion of the body along an interface of the body and the coating multiplied by divided by the rate of erosion of the body in the thickness direction. The same can apply to an anisotropic body having coatings with regions 34 on opposite sides of the body where the regions on opposite sides are aligned along an axis parallel to the direction of preferred erosion E. In other embodiments, such as those having an region-free coating 40 on the opposite side (e.g., the underside 38) of the body 30, the thickness can be up to 50% of the minimum spacing between the plurality of regions multiplied by the average rate of erosion of the body along an interface of the body and the coating divided by the rate of erosion of the body in the thickness direction. For example, some bioerodible polymers erode anisotropically.

The size, spacing, and arrangement of the regions can also control the size of the particles dispensed into the surrounding body fluid. As shown in FIGS. 1D, 2D, 3D, and 4D, different arrangements of the regions combined with different body characteristics can impact the size and shape of the pieces of the eroding endoprosthesis that separate from the reminder of the endoprosthesis once a path erodes through the thickness direction of the body and the coating 32 separates from the body. In some embodiments, the arrangement of regions can vary to ensure that particular parts of a body of an endoprosthesis separate from the remainder of the endoprosthesis in a particular order.

The body 30 includes a bioerodible material (e.g., a bioerodible metal, a bioerodible polymer, a bioerodible ceramic, and/or a bioerodible metal salt). Examples of bioerodible metals suitable for use in the body 30 include magnesium, iron, zinc, and alloys thereof. An example of a suitable bioerodible iron alloy includes Fe-35 Mn. Examples of bioerodible polymers suitable for use as the body 30 include polyglutamic acid, polylactic acid (PLA), poly(ethylene oxide) (PEO), poly-serine, polycaprolactam, poly(lactic-co-glycolic acid) (PLGA), cyclodextrins, polysaccharides (e.g., chitosan and hyaluronan), copolymers thereof, and combinations thereof. Other examples of bioerodible polymers include polyglycolic acid (PGA), polycaprolactone (PCL), polyorthoesters, polydioxanone, poly(trimethylene carbonate) (PTMC), polyphosphazenes, polyketals, proteins (e.g., glycoproteins, fibrin, collagen, gelatin, pectin), polyanhydrides (e.g., poly(ester anhydride)s, fatty acid-based polyanhydrides, amino acid-based polyanhydrides), polyesters, polyester-polyanhydride blends, polycarbonate-polyanhydride blends, and/or combinations thereof. The bioerodible polymers can be blended and/or copolymerized to alter the degradation characteristics.

The coating 32 can include a biocompatible material that can protect the underlying material from erosion. The portion of the coating 32 that separates the plurality of regions 34 can protect the underlying body from contact with physiological fluids at least until the contacted areas of the body erode substantially through the body in the thickness direction. For example, the portion of the coating 32 that separates the plurality of regions 34 can be non-porous. The coating 32 can include bioerodible materials and/or more stable materials. A coating of a bioerodible material can have a slower erosion rate than the body 30. The thickness of the coating 32 can be such that at least a portion of the coating remains non-eroded and on the body 30 at least until the contacted areas of the body erode substantially through the body in the thickness direction. The coating 32 can be between 10 nanometera and 10 microns thick. Examples of suitable bioerodible materials for use in the coating include bioerodible polymers, bioerodible metals, biological materials, and combinations thereof. Suitable bioerodible metals include iron, zinc, and alloys thereof. Suitable bioerodible polymers can include polyglutamic acid, polylactic acid, poly(ethylene oxide), polyserine, polycaprolactam, poly(lactic-co-glycolic acid), cyclodextrins, polysaccharides, copolymers thereof, and combinations thereof. The bioerodible polymers can be blended to alter the degradation characteristics. Suitable biological materials can include collagen, hyaluronic acid, glycoproteins, polysaccharides, pectin, and combinations thereof. In some embodiments, the coating 32 and the body 30 can form a galvanic couple that can allow for the preferential erosion of the body 30 (e.g., the body can act as an anode while the coating acts as a cathode). For example, a magnesium body can have an iron coating so that the magnesium body erodes preferentially.

A coating 32 can also include more stable materials, which can be selected from polymers, metals, ceramics, salts, and biological materials. Examples of relatively stable metals suitable for use in the coating 32 include: tantalum, titanium, cobalt, chromium, stainless steel, cobalt-chromium alloys, platinum enhanced stainless steel alloys, Nitinol alloys, and noble metals, such as platinum, palladium, iridium, and ruthenium. Suitable ceramics can include, for example, CrOx, AlOx, ZrOx, SiOx, TiNOx, and oxides of noble metals such as IrOx. Suitable polymers can included SIBS and PVDF. Suitable biologic materials can include collagen, fibrin, alginates, and polysaccharides. A relatively stable coating 32 can provide a firm substrate to an otherwise eroding structure, thus facilitating endothelial cell growth and/or attachment while retaining sufficient flexibility to facilitate delivery and deployment of the endoprosthesis. Moreover, the visibility of the endoprosthesis to imaging methods, e.g., X-ray and/or Magnetic Resonance Imaging (MRI), can be enhanced, even after the endoprosthesis is partly eroded, by e.g., incorporating a radiopaque material into the coating 32.

The regions 34 allow for a plurality of corresponding areas of the underlying body to be exposed to a physiological environment when the endoprosthesis is implanted in a physiological environment. As shown in FIGS. 1A-1D, 2A-2D, 3A-3D, and 4A-4D, the regions 34 are merely square shaped voids in the coating. The regions 34, however, can have other shapes (e.g., circular, elliptical, polygonal, etc). The size and/or shape of different regions 34 of a single coating 32 can be different or the same. In other embodiments, not shown, the regions 34 can include pores that allow the underlying areas of the body 30 to be contacted by physiological fluids when the endoprosthesis is implanted into a physiological environment. These regions of pores can be surrounded by other portions of the coating 32 that do not allow the underlying surface of the body to be contacted by physiological fluids. For example, a coating 32 having porous regions can be produced by implanting ions in selected regions of the coating, followed by leaching or burning the ions out to create porosity in those selected regions (regions 34). The regions 34, can also include areas of the coating designed to erode to expose underlying areas of the body 30 prior to the erosion of the remainder of the coating 32. The spacing between these regions 34 of faster erosion allow the underlying areas of the body to erode substantially through the body in the thickness direction while at least a portion of the coating remains on the body. For example, the regions 34 can have a substantially thinner thickness than the remainder of the coating, can include a material that erodes at a faster rate than the remainder of the coating, and/or can include a nano/micron scale roughening of the coating that accelerates the erosion rate of the regions 34 versus other portions of the coating 32.

The coating 32 can be deposited on the body 30 of the endoprosthesis by conventional coating techniques or can be created on the surface of a body 30 by modifying the surface of the body 30. Conventional masking, lithographic, and templating techniques can be used to control the placement of the regions 34 in the coating 32. For example, a coating 32 can be produced with a mask made of a set of fine wires or a mesh of a desired pattern. The mask can be set against the inner and/or outer diameters of an endoprosthesis (e.g., a stent), a dense coating of the desired materials can be deposited, and the mask removed.

Lithographic techniques can include soft lithography or nano-sphere (or micro-sphere) lithography. Soft lithography is well suited for nonplanar surfaces and can include techniques such as microcontact printing, replica molding, microtransfer molding, micromolding in capillaries ("MIMIC"), and solvent assisted micromolding ("SAMIM"). Microcontact printing can use a PDMS stamp to print a single molecule thick pattern of ink molecules on a surface of an endoprosthesis. A desired coating material can then be deposited on the surface and a lift process can then be used to remove the coating applied to the inked areas of the endoprosthesis. This can generate a surface including regions of a desired size, spacing, and arrangement corresponding to the printed pattern. The PDMS stamp can be made by conventional photolithography.

Nano-sphere lithography is an effective way to grow periodic and large-area nano-structures. Nano-sphere lithography uses self-assembled nano-spheres (e.g., polystyrene) as a template followed by a deposition process to deposit coating materials in the void spaces between portions of the template. The nanosphere template can be deposited on an endoprosthesis surface by drop coating, spray coating, spin coating, self assembly, sedimentation in a force field, or via crystallization. The nano-spheres can be held to the surface by Van der Waals forces, electro static forces, a thin adhesive layer, and/or plating a thin layer of nickel, titanium, platinum chromium to secure the particles to the stent surface. The deposited template nano-spheres generally assemble in a close packed fashion. The spheres can be isolated by reactive ion etching of the spheres, after deposition, to reduce the sphere diameter and hence isolate the nano-spheres. Once the template has been dried, the void spaces between the templated spheres can be filled with a variety of metals and oxide materials through electrochemical deposition, e.g., by physical vapor deposition ("PVD") or chemical vapor deposition ("CVD"). The void spaces can also be filled with liquid precursor(s) of one or more polymers, sol-gel precursors of a ceramic material, a solution containing an inorganic salt, and/or a dispersion of nano metal or oxide particles to form the coating 32. The coating is formed such that the spheres are partially exposed. Once the coating material is deposited, the spheres can be removed by calcination in air or by dissolution in a chemical solution. Additionally, the spheres can be mixed with biocompatible materials, such as silica or titania, prior to deposition, and the spheres removed prior to the deposition of the coating to produce porous regions surrounded by areas of the coating that protect the underlying body 30 surface area from erosion.

Bioerodible materials can also be used to template the surface of a body of an endoprosthesis. For example, a bioerodible polymer can be deposited onto select regions of the surface of an iron endoprosthesis that correspond to the regions 34 to be formed once the coating material is deposited. The coating material can then be deposited onto the remaining exposed iron surfaces of the endoprosthesis. In other embodiments, the remaining exposed surfaces of the iron endoprosthesis can be modified to create the coating 32. The bioerodible polymer can then be removed. In some embodiments, the bioerodible polymer can remain present as part of the regions 34 and allowed to erode once the endoprosthesis is implanted in a physiological environment. The bioerodible polymer left in the regions 34 to erode in a physiological environment, can include one or more therapeutic agents.

Physical vapor deposition ("PVD") can be used to deposit the coating material. For example, a coating 32 of biocompatible materials, such as iridium oxide, tantalum, titanium, and/or titanium-oxy-nitride, can be deposited onto a bioerodible body, such as magnesium and/or iron, by PVD techniques. The use of PVD techniques can allow the precise placement of regions 34. PVD techniques can also create a coating where the regions 34 are select regions of the coating 32 having a porosity that allows a corresponding area of the body to be exposed to a physiological environment when the endoprosthesis is implanted while the surrounding areas of the coating 32 protect the underlying body surface area from erosion. In some embodiments, a modified Holistic Process Performance Measurement System ("mHPPMS") PVD process can be used to deposit coating 32 onto the body 30 to create a strong bond between the body 30 and the coating 32. A discussion of HPPMS can be found in the following articles, which are hereby incorporated by reference: U. Krausea, M. Lista & H. Fuchsb, *Requiremens of Power Supply Parameters for High-Power Pulsed Magnetron Sputtering,* 392 Thin Solid Films 196-200 (2001) & S. Konstantinidis, J. P. Dauchot & M. Hecq, *Titanium Oxide Thin Films Deposited by High-Power Impulse Magnetron Sputtering,* 515 Thin Solid Films 1182-1186 (2006).

Co-deposition processes can also be used to deposit a coating 32 having regions 34, including a material having a faster erosion rate than the remainder of the coating 32. For example, a relatively stable material, such as tantalum, cobalt, and/or chromium, can be deposited with a bioerodible material, such as magnesium, to create regions 34 including a higher percentage of magnesium than the remainder of the coating 32. Once the magnesium of the composite coating 32 erodes, the regions 34 can allow for the erosion of the underlying material of the body, while the remainder of the coating 32 continues to protect the underlying surface area of the body from erosion. For example, the erosion of the magnesium can leave fine pores through the coating 32 in the areas of the regions 34.

The surface of a bioerodible endoprosthesis can also be modified to create a coating 32. For example, alloying materials can be implanted to produce a relatively stable and/or more slowly eroding material on the surface of an iron, magnesium, or zinc containing endoprosthesis. For example, alloying materials can be implanted on the surface of an iron stent to create a thin coating of stainless steel.

The body 30 and the coating 32 can, in some embodiments, include materials that form a galvanic couple between the body and the coating when the endoprosthesis is implanted in a physiological environment. The body and the coating can be electrically conductive to ensure that the materials of the galvanic couple remain in electrical contact with each other. The galvanic couple, in the presence of ion-containing fluids, such as plasma and/or blood, forms an electrochemical cell in which the body 30 and the coating 32 act as electrodes and the fluid acts as an ion-conducting electrolyte. The galvanic couple can be formed between metals, electrically conductive polymers (e.g., polyvinylidene fluoride, polyaniline, and the like), and electrically conductive polymer composites (e.g., polymer matrices containing electrically conductive particles, wires, meshes, or the like).

The galvanic couple can impact the rate of erosion of overall endoprosthesis, or a portion thereof. For example, a body 30 having a material acting as the galvanic anode and a coating 32 acting as a galvanic cathode can allow for a preferential erosion of the body (e.g., a body 30 including magnesium, zinc, and/or iron with a coating 32 including platinum and/or iridium). The greater the difference in electric potential between the materials of the body and the coating, the greater the preferential erosion of the body. Alternatively, a body having a bioerodible material acting as a cathode and a relatively stable coating acting as an anode can result in a reduced erosion rate for the body.

Figure 5:
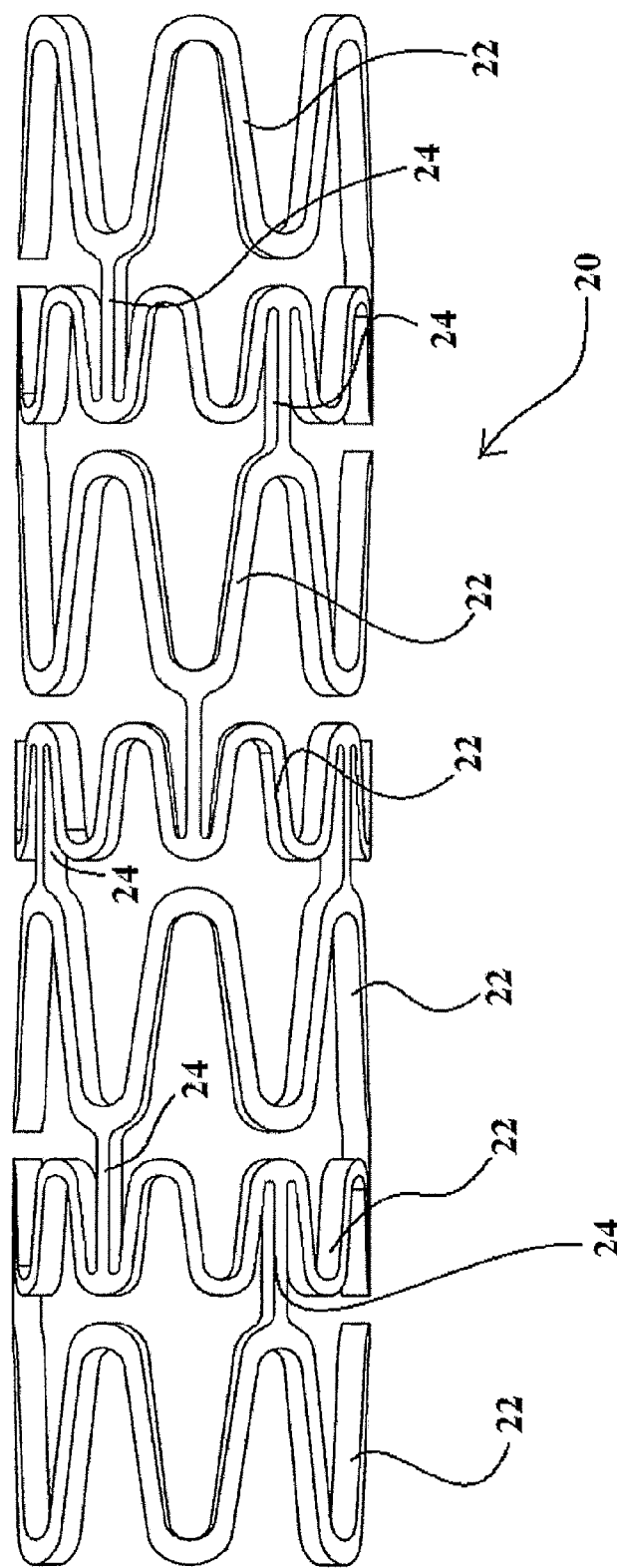
FIG. 5 is a perspective view of an embodiment of an expanded stent.

The endoprosthesis includes a plurality of struts. The struts define a flow passage. One or more of the struts can include a body 30 having a coating 32, as described above. In some embodiments, the endoprosthesis can include a plurality of different struts bodies 30 of different bioerodible materials and/or coatings having regions of different sizes, spacing, arrangements, and/or of different coating materials. For example, the endoprosthesis can be a stent. Referring to FIG. 5, the endoprosthesis can be in the form of a balloon-expandable stent 20. The stent body is in the form of a tubular member defined by a plurality of struts (e.g., the bands 22 and connectors 24). The connectors 24 extend between and connect adjacent bands 22. During use, bands 22 can be expanded from an initial, smaller diameter to a larger diameter to contact the stent 20 against a wall of a vessel, thereby maintaining the patency of the vessel. Connectors 24 can provide the stent 20 with the flexibility and conformability that allow the stent to adapt to the contours of the vessel. The stent 20 defines a flow passage therethrough and is capable of maintaining patency in a blood vessel. In other embodiments, the endoprosthesis can be in the form of a self-expanding stent.

The stent 20 can, in some embodiments, include a plurality of different struts having bodies 30 of different bioerodible materials and/or coatings having regions of different sizes, spacing, arrangements, and/or of different coating materials. For example, an iron stent can have different struts having different coatings 32 over bodies of iron. One coating can have a pattern of regions designed to decrease the overall erosion rate of the strut relative to the remainder of the stent 20. Additionally, one or more struts could include a coating of a material to increase the overall erosion rate of the one or more struts relative to uncoated iron struts. For example, the erosion rate increasing coating can act as a galvanic cathode to increase the erosion rate of the strut. Each coating can include a coating material and a pattern of regions designed to effect a particular erosion rate for each strut. For example, connectors 24 can be designed to erode prior to the erosion of the bands 22. In other embodiments, selected regions of the stent 20, each including a plurality of bands and connectors, can have different coatings 32, and perhaps select regions without any coating, to produce a stent 20 that erodes to produce a shorter stent 20 prior to complete erosion.

Stent 20 can be of any desired shape and size (e.g., superficial femoral artery stents, coronary stents, aortic stents, peripheral vascular stents, gastrointestinal stents, urology stents, and neurology stents). Depending on the application, the stent can have a diameter of between, for example, 1 mm to 46 mm. In certain embodiments, a coronary stent can have an expanded diameter of from 2 mm to 6 mm. In some embodiments, a peripheral stent can have an expanded diameter of from 5 mm to 24 mm. In certain embodiments, a gastrointestinal and/or urology stent can have an expanded diameter of from 6 mm to about 30 mm. In some embodiments, a neurology stent can have an expanded diameter of from about 1 mm to about 12 mm. An Abdominal Aortic Aneurysm (AAA) stent and a Thoracic Aortic Aneurysm (TAA) stent can have a diameter from about 20 mm to about 46 mm.

Figure 6A:
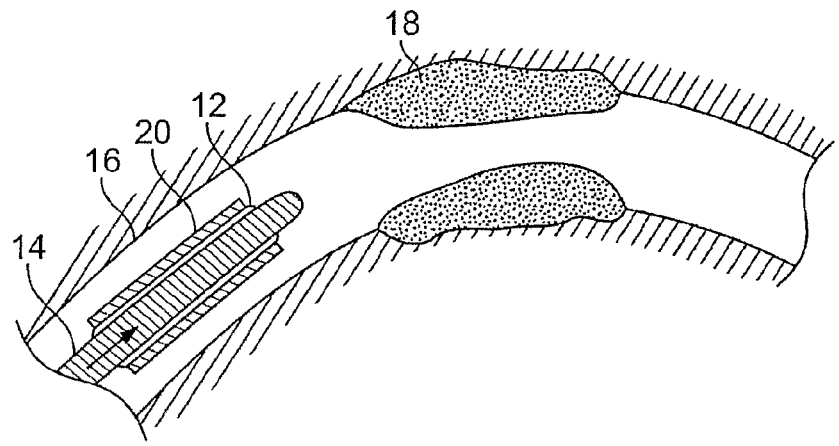
FIGS. 6A-6C are longitudinal cross-sectional views illustrating delivery of a stent in a collapsed state, expansion of the stent, and deployment of the stent.
Figure 6B:
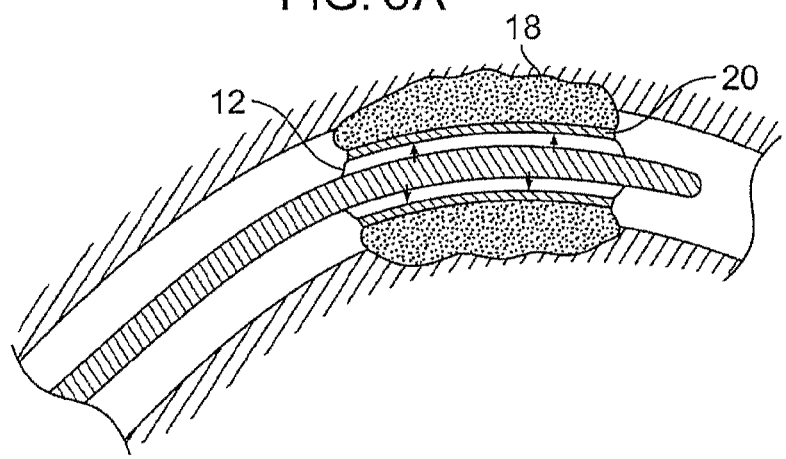
Figure 6C:
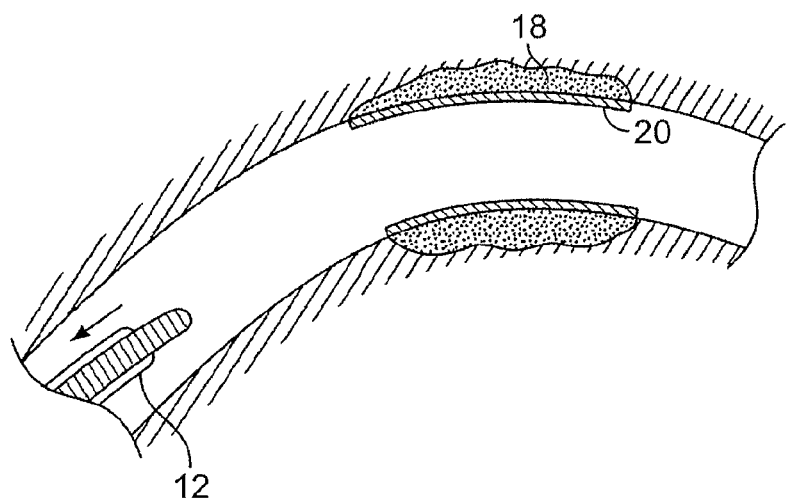

Stents can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Sentinol® system, available from Boston Scientific Scimed, Maple Grove, Minn. Referring to FIGS. 6A-6C, a balloon-expandable stent 20 can be placed over a balloon 12 carried near a distal end of a catheter 14, and directed through the lumen 16 (FIG. 6A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 6B). The pressure is then released from the balloon and the catheter is withdrawn from the vessel (FIG. 6C).

In some embodiments, stents can also be a part of a covered stent or a stent-graft. In other embodiments, a stent can include and/or be attached to a biocompatible, non-porous or semi-porous polymer matrix made of polytetrafluoroethylene (PTFE), expanded PTFE, polyethylene, urethane, or polypropylene.

In some embodiments, stents can be formed by fabricating a wire having a bioerodible body and a coating including a plurality of the above described regions, and knitting and/or weaving the wire into a tubular member.

In some embodiments, stents can include therapeutic agents incorporated into one or more portions of the body 30 and/or the coating 32 (including the regions 34). Stents can also include additional drug eluding layers and/or deposits of therapeutic agents.

A number of embodiments have been described. Nevertheless, it will be understood that various modifications may be made without departing from the spirit and scope of this disclosure. Accordingly, other embodiments are within the scope of the following claims.

What is claimed is:

1. An endoprosthesis comprising a plurality of struts defining a flow passage, at least one strut comprising:
   (a) a body comprising a bioerodible material having a thickness, and
   (b) a coating overlying the body, the coating comprising a plurality of regions that allow physiological fluids to contact a plurality of corresponding areas of the underlying body when the endoprosthesis is implanted in a physiological environment, the plurality of regions being sized and arranged so that the contacted areas of the body erode substantially through the body in the thickness direction while the coating remains on the body when the endoprosthesis is implanted in the physiological environment, wherein a rate of erosion of the body in the thickness direction multiplied by the thickness of the body is less than a rate of erosion of the body along an interface between the body and the coating multiplied by the distance between adjacent regions thereby producing undercut regions.

2. The endoprosthesis of claim 1, wherein the bioerodible material erodes isotropically.

3. The endoprosthesis of claim 2, wherein the plurality of regions are arranged such that the distance between adjacent regions is equal to at least the thickness of the body.

4. The endoprosthesis of claim 2, wherein the plurality of regions are arranged such that the distance between adjacent regions is equal to at least twice the thickness of the body.

5. The endoprosthesis of claim 1, wherein the bioerodible material erodes anisotropically.

6. The endoprosthesis of claim 1, wherein a rate of erosion of the body in the thickness direction multiplied by the thickness of the body is less than a rate of erosion of the body along an interface between the body and the coating multiplied by ½ of the distance between adjacent regions.

7. The endoprosthesis of claim 1, wherein the bioerodible material has a first electric potential and the coating has a second electric potential different from the first electric potential so that the body and the coating form a galvanic couple when the endoprosthesis is implanted in a physiological environment.

8. The endoprosthesis of claim 7, wherein the first electric potential is less than the second electrode potential so that the body acts as an anode and the coating acts as a cathode when the endoprosthesis is implanted in a physiological environment.

9. The endoprosthesis of claim 7, wherein the bioerodible material of the body is a bioerodible metal selected from the group consisting of magnesium, iron, zinc, and alloys thereof and the coating comprises a metal selected from the group consisting of platinum, iridium, and alloys thereof.

10. The endoprosthesis of claim 7, wherein the first electric potential is greater than the second electrode potential so that the body acts as a cathode and the coating acts as an anode when the endoprosthesis is implanted in a physiological environment.

11. The endoprosthesis of claim 1, wherein the bioerodible material of the body is a bioerodible metal selected from the group consisting of magnesium, iron, zinc, and alloys thereof.

12. The endoprosthesis of claim 1, wherein the body comprises a bioerodible polymer selected from the group consisting of polyglutamic acid, poly(ethylene oxide), polycaprolactam, poly(lactic-co-glycolic acid), polysaccharides, and combinations thereof.

13. The endoprosthesis of claim 1, wherein the coating surrounds the circumference of the body.

14. The endoprosthesis of claim 1, wherein the coating partially surrounds the circumference of the body.

15. The endoprosthesis of claim 1, wherein the regions comprise voids in the coating.

16. The endoprosthesis of claim 1, wherein the regions comprise pores in the coating.

17. The endoprosthesis of claim 1, wherein the regions have a higher erosion rate than the remainder of the coating in a physiological environment.

18. The endoprosthesis of claim 1, wherein the coating comprises a bioerodible material having a slower erosion rate than the bioerodible material of the body.

19. The endoprosthesis of claim 1, wherein the endoprosthesis is a stent.

* * * * *